(12) United States Patent
Varga et al.

(10) Patent No.: US 12,229,382 B2
(45) Date of Patent: *Feb. 18, 2025

(54) SYSTEM AND METHOD FOR GENERATING A VIRTUAL REALITY INTERFACE FOR DISPLAYING PATIENT HEALTH DATA

(71) Applicant: Vyaire Medical, Inc., Mettawa, IL (US)

(72) Inventors: Christopher M. Varga, Laguna Hills, CA (US); Terry Blansfield, Orange, CA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 63 days.

This patent is subject to a terminal disclaimer.

(21) Appl. No.: 18/118,088

(22) Filed: Mar. 6, 2023

(65) Prior Publication Data

US 2023/0205390 A1 Jun. 29, 2023

Related U.S. Application Data

(63) Continuation of application No. 16/557,910, filed on Aug. 30, 2019, now Pat. No. 11,599,238.
(Continued)

(51) Int. Cl.
*G06F 3/04815* (2022.01)
*A61B 5/00* (2006.01)
(Continued)

(52) U.S. Cl.
CPC .......... *G06F 3/04815* (2013.01); *A61B 5/743* (2013.01); *G06F 3/017* (2013.01);
(Continued)

(58) Field of Classification Search
CPC .. G06F 3/04815; G06F 3/017; G06F 3/04817; G06F 3/0482; G06F 2203/04802;
(Continued)

(56) References Cited

U.S. PATENT DOCUMENTS 6,032,119 A 2/2000 Brown et al.
9,218,671 B2 12/2015 Carnes
(Continued)

OTHER PUBLICATIONS

International Search Report and Written Opinion for Application No. PCT/US2020/026273, dated Aug. 3, 2020, 21 pages.
(Continued)

*Primary Examiner* — Kenny Nguyen
(74) *Attorney, Agent, or Firm* — Morgan, Lewis & Bockius LLP

(57) ABSTRACT

The disclosed system generates a three dimensional virtual space that includes an object representation of at least a portion of a human body and a first three-dimensional cylindrical surface floating within the three-dimensional space, wherein the first three-dimensional cylindrical surface includes a two-dimensional data area for a presentation of data to a user viewing the first three-dimensional cylindrical surface in the three-dimensional space. A two-dimensional data representation of first physiological data is displayed on the two-dimensional data area. In response to receiving a user selection of a portion of the three-dimensional cylindrical surface, the system generates one or more additional surfaces floating within the three-dimensional space. A two-dimensional data representation of second physiological data associated with the first physiological data is displayed on a data area of the one or more additional surfaces.

20 Claims, 21 Drawing Sheets

Related U.S. Application Data

(60) Provisional application No. 62/828,365, filed on Apr. 2, 2019.

(51) Int. Cl.
  *G06F 3/01*       (2006.01)
  *G06F 3/04817*    (2022.01)
  *G06F 3/0482*     (2013.01)
  *G06T 19/00*      (2011.01)
  *G06V 20/20*      (2022.01)
  *G16H 30/20*      (2018.01)
  *G16H 40/63*      (2018.01)

(52) U.S. Cl.
  CPC ........ *G06F 3/04817* (2013.01); *G06F 3/0482* (2013.01); *G06T 19/006* (2013.01); *G06V 20/20* (2022.01); *G16H 30/20* (2018.01); *G16H 40/63* (2018.01); *G06F 2203/04802* (2013.01)

(58) Field of Classification Search
  CPC ....... A61B 5/743; G06T 19/006; G06T 19/00; G06V 20/20; G16H 30/20; G16H 40/63; G16H 15/00; G16H 10/60
  See application file for complete search history.

(56) References Cited

U.S. PATENT DOCUMENTS

| | | | |
|---|---|---|---|
| 9,508,195 B2 * | 11/2016 | Heuvel | G06T 19/006 |
| 9,734,779 B2 * | 8/2017 | Forutanpour | G09F 9/301 |
| 9,747,015 B2 * | 8/2017 | Forutanpour | G06F 3/04842 |
| 9,792,567 B2 | 10/2017 | Khasis | |
| 10,068,057 B2 | 9/2018 | Moore | |
| 10,430,738 B2 | 10/2019 | Khasis | |
| 11,853,533 B1 * | 12/2023 | Chor | G06F 3/0484 |
| 2011/0047459 A1 | 2/2011 | Van Der Westhuizen et al. | |
| 2011/0071818 A1 | 3/2011 | Jiang | |
| 2013/0151965 A1 | 6/2013 | Demiris | |
| 2013/0181952 A1 | 7/2013 | Lin | |
| 2013/0246967 A1 * | 9/2013 | Wheeler | G06F 3/012 715/784 |
| 2014/0002419 A1 | 1/2014 | Thorson | |
| 2014/0022256 A1 | 1/2014 | Carnes | |
| 2014/0249856 A1 | 9/2014 | Moore | |
| 2014/0250405 A1 | 9/2014 | Wheeler | |
| 2015/0160856 A1 | 6/2015 | Jang | |
| 2015/0261925 A1 | 9/2015 | Wang et al. | |
| 2015/0363071 A1 | 12/2015 | Devale | |
| 2016/0026308 A1 | 1/2016 | Wu | |
| 2016/0063762 A1 * | 3/2016 | Heuvel | G06F 3/011 345/633 |
| 2016/0239190 A1 * | 8/2016 | Forutanpour | G06F 1/1652 |
| 2016/0240154 A1 * | 8/2016 | Forutanpour | G09G 3/3644 |
| 2017/0262786 A1 | 9/2017 | Khasis | |
| 2017/0277136 A1 | 9/2017 | Minami | |
| 2017/0329511 A1 | 11/2017 | Ueno | |
| 2017/0351992 A1 | 12/2017 | Khasis | |
| 2018/0004391 A1 | 1/2018 | Rao | |
| 2018/0124385 A1 | 5/2018 | Van Beek | |
| 2019/0138183 A1 | 5/2019 | Rosas | |
| 2019/0139426 A1 | 5/2019 | Kesavadas | |
| 2019/0250699 A1 | 8/2019 | Mulase | |
| 2019/0282324 A1 | 9/2019 | Freeman | |
| 2019/0302460 A1 | 10/2019 | Kaul | |
| 2019/0355447 A1 | 11/2019 | Barkol | |

OTHER PUBLICATIONS

European Office Action for Application No. 20722076.5, dated Jul. 4, 2024, 8 pages.

* cited by examiner

SYSTEM AND METHOD FOR GENERATING A VIRTUAL REALITY INTERFACE FOR DISPLAYING PATIENT HEALTH DATA

CROSS-REFERENCE TO RELATED APPLICATIONS

This application is a continuation of application Ser. No. 16/557,910, filed on Aug. 30, 2019, now U.S. Patent No. 11,599,238, which claims the benefit of Provisional Application No. 62/828,365, filed on Apr. 2, 2019, the entirety of each of which is incorporated herein by reference for all purposes.

BACKGROUND FIELD

The subject technology addresses deficiencies commonly encountered in hospital care and medical care user and system interfaces and display of patient and patient population-based health data.

SUMMARY

Existing systems and visual presentations (e.g., screen layouts) are not conducive to consolidation and simplification of critical patient information and/or comprehensive visual presentation of a patient or patient population condition with time-scrubbing capability and presentation of event-related data. For example, for a clinician to ascertain a patient condition from data residing in multiple devices or systems, the clinician may interact with or navigate each of these systems or data sources separately and then integrate the data sources manually or read these data from dashboard-style visual elements, and/or through navigation of multiple screens, systems, windows, panes, lists or combinations thereof. Furthermore, the ability to time-relate events or data elements is not straightforward nor enabled by these visualization tools. For example, if a clinician notes that a ventilator parameter was in a state that required attention at a certain time or was in a range which was flagged/marked for clinical reasons, if the clinician desires to see what was happening in the patient's lab data (e.g., blood panel) at that same time point the clinician may have to search for that data manually and once found, that data may not be provided in a manner that would facilitate viewing alongside or in sight of the associated ventilator event. Time sequences of medical patient data or patient population data are also not typically presented in a graphical way that can be manipulated appropriately within the context of other medical data sources that may or may not be related.

Challenges associated with presenting multiple data elements from multiple data sources in a single collection of visual elements are magnified by the two-dimensionality of most visual presentations. For example, presentation of time trends of patient data are typically executed in a linear or rectangular fashion which frequently leads to crowding of visual elements and unreadable small data plots as additional data sources are added to a fixed screen or visual presentation space (e.g., monitor, tablet screen). Accordingly, there is a need for an improved visual presentation layer or element and methodology of presentation for patient health and population health data which can remedy these deficiencies.

In one aspect, the subject technology provides three dimensional visual elements and structures for presentation of patient health and population health data. In this regard, the subject technology comprises a three dimensional visual health data element that combines time-related health data for individual patient diagnostic and/or therapeutic systems (e.g., ventilation, laboratory tests, medication infusion, etc.). The health data element is visualized in the form of a rotatable, extendable, and configurable cylindrical structure. This structure provides for visual time-alignment of critical patient data and patient flags/markers related to important aspects of a patient condition. For example, markers related to weaning from ventilation, sedation levels, lung protection, and others are visually combined by the subject technology to transform separate data sources into a single comprehensive visual indicator of the patient condition or patient population status. According to various aspects, the visual cylindrical health data element substantially surrounds an object representation of at least a portion of a human body—which together provide an integrated visual touch point and flag/marker/event indicator. The object representation may include, for example, a visual representation of the related patient. Markers/flags/events are defined within each system for the patient (e.g., respiratory, sedation, laboratory, infusion, vitals) and represent patient data points which are either outside of normal values, outside of defined protocols, not within certain thresholds or conversely within certain important clinical bounds (e.g., for events). As a clinician, it is essential to get a holistic view of a patient's condition and the cylindrical structure or structures of this disclosure enable this centralized view.

According to various implementations, the disclosed system generates a three dimensional virtual space that includes an object representation of at least a portion of a human body and a first three-dimensional cylindrical surface floating within the three-dimensional space, wherein the first three-dimensional cylindrical surface includes a two-dimensional data area for a presentation of data to a user viewing the first three-dimensional cylindrical surface in the three-dimensional space. A two-dimensional data representation of first physiological data is displayed on the two-dimensional data area. In response to receiving a user selection of a portion of the three-dimensional cylindrical surface, the system generates one or more additional surfaces floating within the three-dimensional space. A two-dimensional data representation of second physiological data associated with the first physiological data is displayed on a data area of the one or more additional surfaces.

In some implementations, the one or more additional surfaces include one or more additional three-dimensional surfaces and, in response to receiving the user selection, the one or more additional three-dimensional cylindrical surfaces floating within the three-dimensional space are generated. A two-dimensional data representation of second physiological data associated with the first physiological data may be displayed on a data area of the one or more additional three-dimensional cylindrical surfaces. The one or more additional three-dimensional cylindrical surfaces may be displayed above or below and adjacent to the first three-dimensional cylindrical surface, with each additional three-dimensional cylindrical surface being circumscribed about the portion of the object representation. Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

DESCRIPTION

Figure 1:
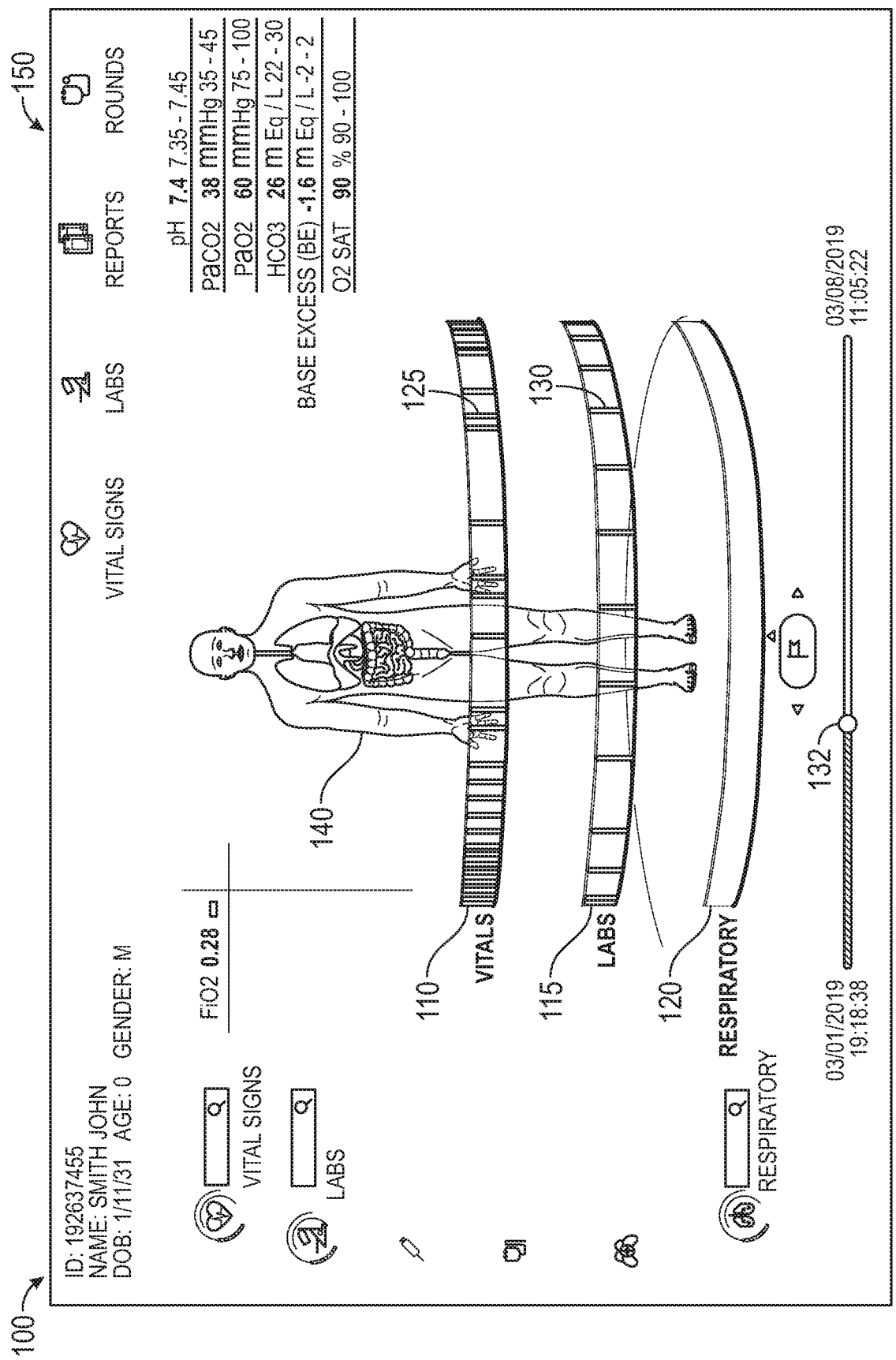
FIG. 1 depicts example virtual reality interface for the display of patient health data, including visual cylindrical health data elements substantially surrounding a visual representation of a patient, with each element represented as a cylindrical band with health-related flags/markers superimposed thereon, according to various aspects of the subject technology.

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

The subject technology addresses various challenges related to managing patients that exist in hospital and other medical environments where a lot of different data sources are available or required to make clinical decisions. Multiple devices may contribute to a patient's care. For example, the intensive care unit may utilize ventilators, infusion pumps, cardiac equipment, and various sensors. Additionally, clinicians may rely on a substantial amount of lab data in the form of, for example, patient electronic medical records, test results, etc. Clinicians (e.g., respiratory therapists, nurses, doctors) are often forced to search for information in different systems to put together a story about a patient to navigate and manage patient care. Each type of data and/or system may be viewed in isolation in one particular area without a way to time align or assimilate with other data feeds.

The subject technology addresses the foregoing problems by aggregating disparate data into a three dimensional (3D) centralized representation of patient data structures, and which allows a clinician to visualize patient data in a time-aligned manner and in a way that indicates how each portion of data (retrieved from the multiple data sources) relate to each other. Thus, a clinician may view all of the data without having to switch between different data sources, or between panels or screens or tabs, as is done in traditional systems. The subject technology provides the data superimposed onto a 3D cylindrical structure, within a virtual 3D space. The 3D cylindrical structure may include multiple cylinders, with each cylinder providing one or more data sets for review in the 3D space. Each cylinder can be rotated infinitely to review, in embodiments, a time-aligned data set provided by the cylinder, and multiple cylinders may be stacked as bands or rings of different data sets on top of one another.

FIGS. 1 through 5 depict various views of an example virtual reality interface for the display of patient health data, including visual cylindrical health data elements substantially surrounding a visual representation of a patient, with each element represented as a three dimensional floating cylindrical band with health-related flags/markers superimposed thereon. For the purpose of this disclosure, the terms cylindrical "elements" and cylindrical "bands" may be used interchangeably when describing the disclosed cylindrical structures floating in the 3D space.

The virtual reality interface described herein is implemented by computer software and visually presented as three dimensional objects within a three dimensional space. According to various aspects, the disclosed three dimensional cylindrical data elements may be manipulated in the three dimensional space by user input. The user input may be, for example, by way of a touch screen to manipulate the elements by sensing user input on an area of the touch screen corresponding to the display of the elements. The virtual reality interface may also be visually presented in an augmented reality system, whereby one or more users may view the virtual reality interface using augmented reality viewing technology. With brief reference to FIGS. 16 and 17, the virtual reality interfaces depicted herein may be displayed on a display screen 1706 of a computing device 1700 operably connected to the centralized server 1710. Patient data is stored in one or more data sources (e.g., a database) in real time and managed by a centralized server 1710. The centralized server aggregates the real time patient data and provides the data for display by computing device 1700 in real time.

FIG. 1 depicts an example virtual reality interface 100 for the display of patient health data. A visual cylindrical data element 110, visual cylindrical data element 115, and visual cylindrical data element 120 are included in the depicted virtual reality interface 100.

Each cylindrical data element 110, 115, 120 is displayed responsive to a prior selection of data and corresponds to the data selected. For example, data element 110 includes patient vitals data, data element 115 includes lab data, and data element 120 includes respiratory data. Each data element may be configured to obtain its data from a respective data source or multiple data sources. According to various implementations, interface 100 may include a configuration screen (not shown) which allows a user to indicate and/or or select which types of data may be displayed on interface 100. Interface 100 may then render respective cylindrical data elements for the respective selected data types. In some implementations, the cylindrical data elements may be configured or reconfigured to display a particular type of data based on a predetermined type of user selection (e.g., a right click, or tap-and-hold gesture) of the element within the 3D space which brings about a dialog for selection between available data types. In some implementations, the cylindrical data elements may be configured to display data based upon a user profile, clinical specialty, patient type, disease state, facility type or care area.

Each of the aforementioned individual cylindrical data elements display time-related patient data that include flags or markers which may be displayed alongside of the patient data for viewing. For example, a flag/marker 125 is included in the visual cylindrical data element 110, and a flag/marker 130 is included in the visual cylindrical data element 115. For the purpose of this disclosure, the terms "flag"/"flagged" and "marker"/"marked" may be used interchangeably. According to various implementations, flagged (or marked) portions on the 3D cylinders may indicate data points for further review. Data can be marked by way of a gesture, or marked automatically when the data satisfies or exceeds a threshold, or predetermined range. A marker may appear on a cylinder, behind corresponding data, in a different color (e.g., green, yellow, red, etc.) than the data and/or the cylinder. In this regard, the cylinder, data, and/or marker itself may be colored to indicate a level of importance or the data source from which the data came from. As depicted in FIG. 1, a marker may appear as a vertical stripe (e.g., in red) and have a thickness corresponding to a time element of the data.

A marker may be selected, for example, by a gesture at or near the marker such as a tap on the marker or a swipe over the marker. As will be described further, selecting a marker may expand the data at the marker. In this regard, further data representative of the marker may be displayed on another cylindrical band that appears above or below the current band, or may be displayed on the current band or proximate to the current band as a separate callout or dialog of data. Additionally or in the alternative, selecting a marker specific to one data stream (e.g., volume or pressure, heart rate, etc.) and that corresponds to individual data that's flagged or out of range may cause the display of a secondary band on the band that is colored underneath the data set.

Each cylindrical data element 110, 115, 120 may take the form of a semi-circle or, according to some aspects, may take the form of a closed or complete circle or ellipse. The axis of cylindrical data element 110, 115, 120 may define a point of rotation such that the element may be caused to freely rotate about the axis (from right to left or left to right). As depicted in FIGS. 1 through 5, virtual interface 100 may include a graphical slider 132 which, when activated in a direction (e.g., slid horizontally to the left or right), will rotate the displayed cylinders according to the direction the graphical slider 132 is moved. In some implementations, only cylinders that are preselected may rotate as slider 132 is moved. Selection may be by way of touch gesture to highlight a cylinder prior to selection or by activating the cylinder for rotation by way of setting a visual flag corresponding to the cylinder (e.g., a checkbox). In this regard, a cylinder to be rotated by slider 132 may be locked or unlocked to rotate with or independently of, respectively, another cylinder, as described further below. Each cylindrical data element may circumscribe an object representative of at least a portion of a human body. As depicted in FIGS. 1 through 5, the object may be a 3D representation of a human body 140.

Virtual reality interface 100 may further include a virtual listing 150 of one or more selected patient data values. Virtual listing 150 may appear within the 3D space over the rings and/or to a side of the object 140. In some implementations, the virtual listing 150 may replace object 140 on the axis of the cylindrical data elements. Each patient data value displayed in virtual listing 150 may be a current value of a measured physiological parameter (e.g., last measured blood pressure, temperature, oxygen level, etc.). In this regard, a patient data value may change color or become highlighted or otherwise flagged upon the data value satisfying a predetermined threshold (e.g., exceeding a limit for the physiological parameter). The patient data values displayed in virtual listing 150 may be selected by a user or, in some implementations, automatically display based on the display of a cylindrical element displaying the corresponding data for the data value. For example, cylindrical data element 120 may display a real time inspiratory flow over a period of time, and the current corresponding data value of the real time inspiratory flow may be displayed in listing 150.

In some implementations, the representation of the human body 140 (or portion thereof) may appear adjacent to the cylindrical structure rather than surrounded by the cylindrical structure, and the body may also move into or out of the virtual space based upon data visualization. In some implementations, object representation 140 may be manually or automatically (e.g., based on machine learning) zoomed to a portion that is relevant to the data being shown, or may be replaced by only a portion of the body relevant to the data (or marker, as described below) for more detailed visualization. For example, if respiratory data is being reviewed, a full body may be replaced by just the chest region, including the lungs, to show in greater detail the areas of concern or interest, or that correspond to a given therapy or generated markers.

Figure 2:
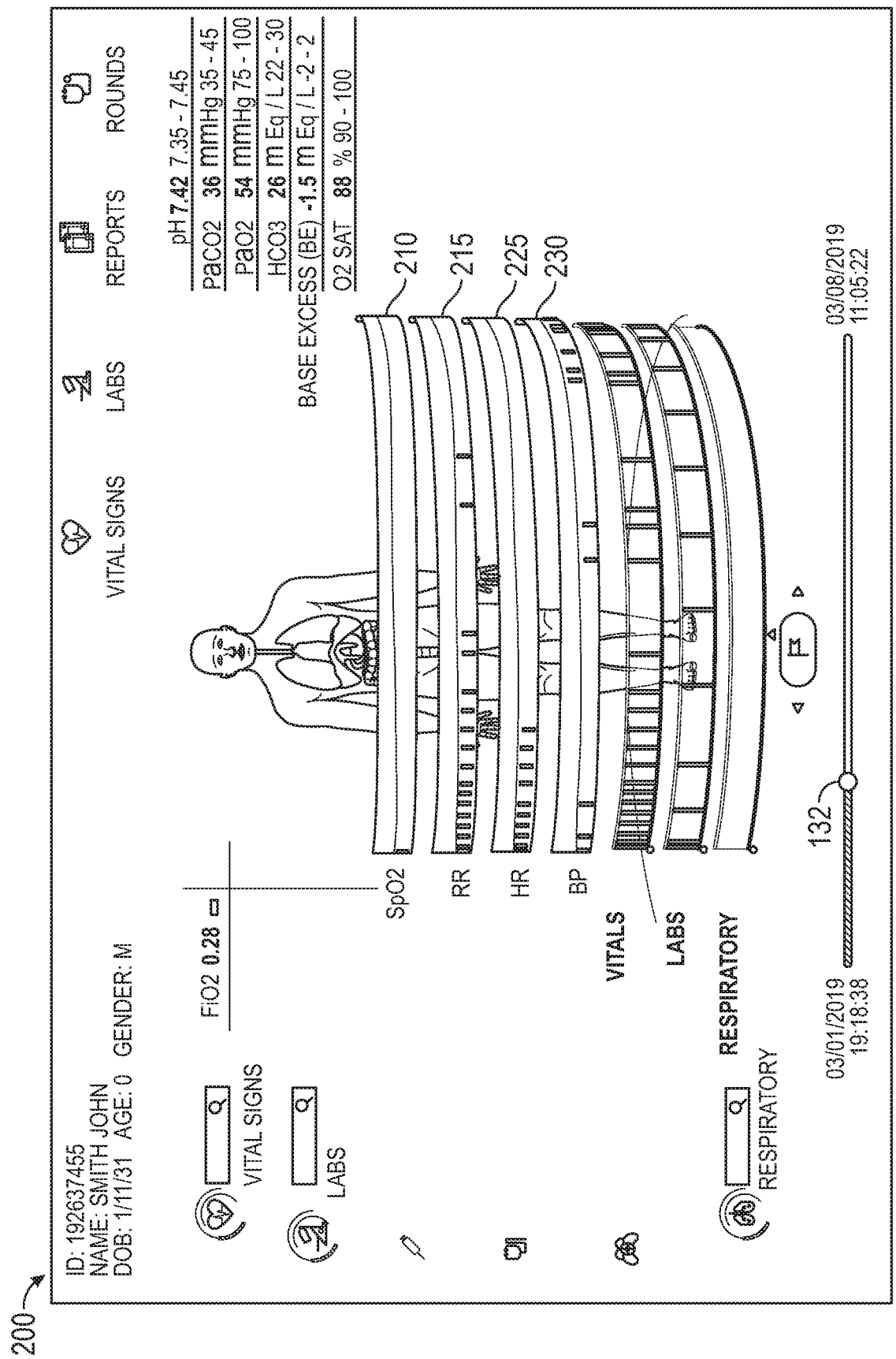
FIG. 2 depicts a further virtual reality interface, including cylindrical bands with data flags/markers, according to various aspects of the subject technology.

FIG. 2 depicts a further example virtual reality interface 200, including cylindrical bands with data flags/markers, according to various aspects of the subject technology. The example of FIG. 2 includes additional graphical elements to those discussed in FIG. 1 above. As illustrated, FIG. 2 includes additional three-dimensional cylindrical surfaces 210, 215, 225, and 230 floating within a three-dimensional space of the virtual reality interface 200. FIG. 2 is discussed in more detail below.

Figure 3:
FIG. 3 depicts a further virtual reality interface, including cylindrical bands with data and flags/markers and neonatal visual patient, according to various aspects of the subject technology.

FIG. 3 depicts a further example virtual reality interface 300, including cylindrical bands with data and flags/markers and neonatal patient representation, according to various aspects of the subject technology. As illustrated, a visual cylindrical data element 340, and visual cylindrical data element 345 are included in the virtual reality interface 300. FIG. 3 includes additional three-dimensional cylindrical surfaces 310, 315, 325, 330, and 335 floating within a three-dimensional space of the virtual reality interface 300. FIG. 3 is discussed in more detail below.

Figure 4:
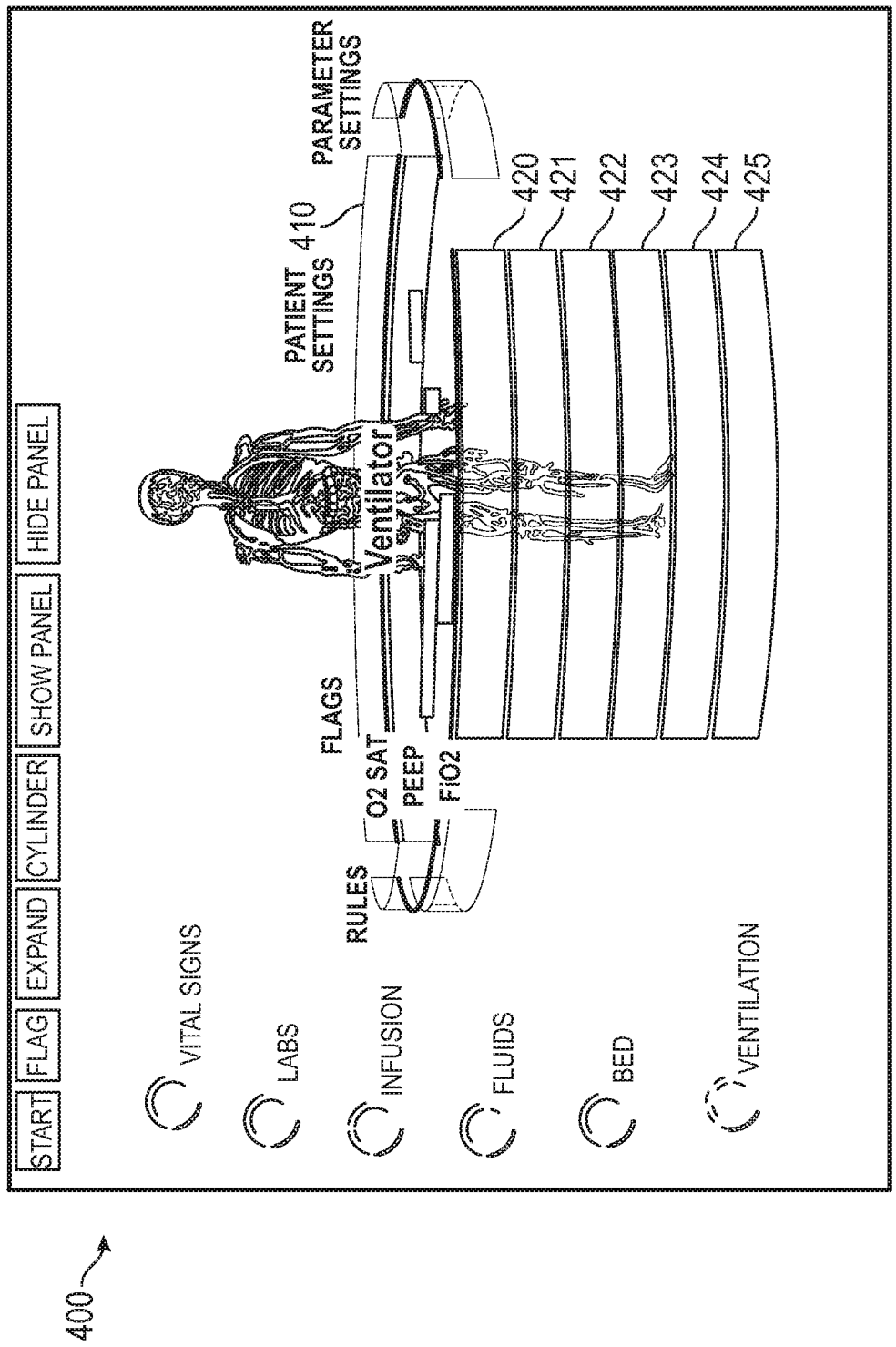
FIG. 4 depicts an example virtual reality interface, including a segmented cylindrical health data element surrounding a patient at a single raised level, with a selected segmented band providing further data panels/bands to display additional corresponding patient data, according to various aspects of the subject technology.

FIG. 4 depicts a further example virtual reality interface 400, including a segmented cylindrical health data element 410 surrounding a patient at a single raised level, with a selected segmented band providing further data panels/bands to display additional corresponding patient data, according to various aspects of the subject technology. In the depicted example, the segmented bands circumscribe an axis in the 3D space, with each band being separated from each other by an open space. In this regard, each segmented band may display a different type of data (e.g., from a different data source). A segmented band 420 may be selected by a user to generate further data panels/bands 421, 422, 423, 424, 425 below or above it for the display of additional corresponding patient data. The newly displayed bands and data may be associated with the selected band. For example, when a user selection is received at a first band of the segmented bands, the system may be configured to display one or more additional three-dimensional cylindrical surfaces to be displayed above or below the first band in a curvilinear plane aligned with a curvilinear plane of the first band. In one example, band 420 may include a variety of event flags over a period of time and, by using a predetermined gesture (e.g., a tap-hold-and-drag), a user may cause the display of bands 421, 422, 423, 424, 425 which each respectively display data that corresponds to each respective data flag indicated in band 420.

Figure 5:
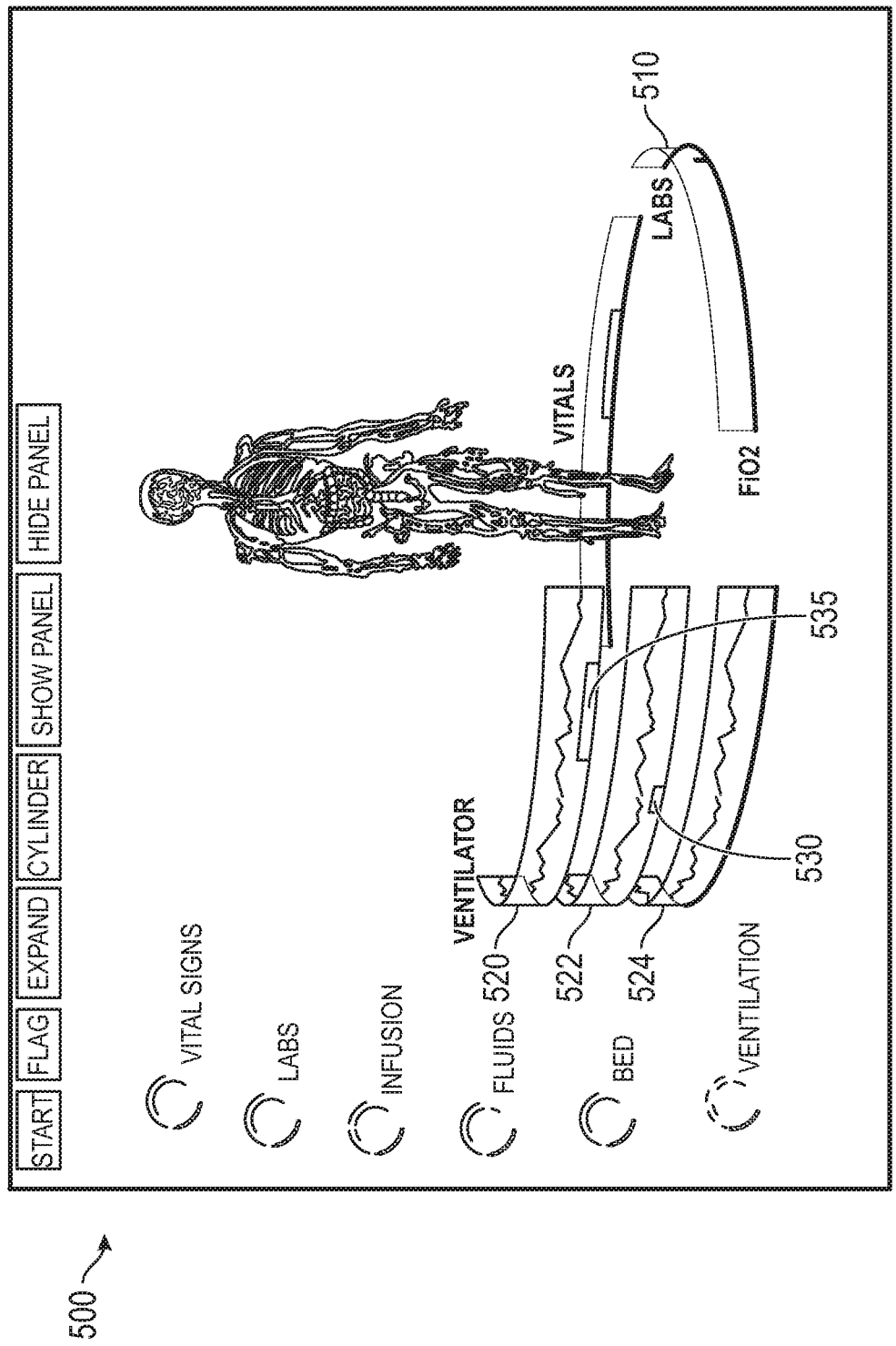
FIG. 5 depicts an example virtual reality interface, including a segmented cylindrical health data element surrounding a patient at a single base level, with a selected segmented band providing further data panels/bands to display additional corresponding patient data, according to various aspects of the subject technology.

FIG. 5 depicts a further example virtual reality interface 500, including a segmented cylindrical health data element 510 surrounding a patient at a single base level, with a selected segmented band providing further data panels/bands 520, 522, and 524 to display additional corresponding patient data, according to various aspects of the subject technology. As further illustrated, the data panel 520 includes a secondary band 530 that is colored underneath the data set shown in the data panel 520. Since each cylindrical data element may be time based in that the data displayed by the element is displayed across the element according to a time scale, secondary band 530 may represent a period of time according to the length of secondary band across the same time scale. Secondary band 530 may indicate a section of data that has been flagged for further review (e.g., by the user or by the disclosed machine learning algorithm) or may indicate that an event took place during the flagged period of time. Also, the data panel 522 includes a secondary band 530 that is colored underneath the data set shown in the data panel 522.

As described previously with reference to FIGS. 1 through 5, a visual cylindrical data element is constructed of cylindrical segments or bands which can display health-system, body-system or device data, flags, images, events and can be static in time or can be time-scaled. The cylindrical bands can be manipulated individually or in groups, can be time-locked to other cylinders, can be re-arranged, swapped or customized. According to various implementations, when a band becomes time-locked, the band may become vertically aligned in time such that if two bands are viewed together they are using the same time scale and they are aligned by time such that if one band is rotated to scroll through time, the other bands will rotate along with it to stay in alignment so events may be viewed in different systems (e.g., bands) that occurred at the same time. In this regard, if a band is unlocked, it can be rotated independently of the other bands and will be out of time-alignment until re-locked in which case it will rotate back into time alignment with other bands.

Individual cylindrical bands which display time-related patient data can additionally contain flags or markers which are displayed alongside the data for easy viewing. Implementations of the visual structure can also contain a separated or integrated flag/marker/event advance button or icon which allows the user to quickly move through patient flags/markers/events by advancing incrementally through flags with other data or system bands moving in time alignment. Alternatively, the bands can move independently using the advance button if the cylindrical band stack is unlocked. In this case only a highlighted band may advance from flag/marker/event to flag/marker/event while other bands may remain stationary with current values. According to various implementations, advancement between markers/events/flags can also be achieved using a selector wheel or other rotational structure or band.

Cylindrical segments/bands can represent any time period of interest, for example, the time from admission to the current time or the previous 24 hours. The time period may be selectable using a selection cylinder or other selection means to determine a time-period of interest for visualization. Visual indicators for markers/flags/events can be comprised of lines or solid bars or tabs with magnitudes that correspond to the time a value is marked. Alternative visual markers are also within the scope of this disclosure. If a user is interested in seeing trends of particular values, the user can expand one or more bands of a given system into individual cylindrical segments which contain trend graphs for the time period of interest. As an example, a user interested in viewing ventilation or respiratory-related patient data can select a stack of cylindrical bands with PEEP, respiratory rate, tidal volume, EtCO2 etc. Alternatively, trend graphs for data from different systems can be mixed and matched. The cylinder band stack can be customizable or can be selected from defaults or alternatively can be automatically stacked and selected by intelligent rules that present the user with the most appropriate patient information relevant to their current condition. The height and circumferential extent of the visual cylindrical element can be infinite as values can be populated onto the bands as the bands come into view during rotation or when the cylinder is moved up or down. Individual cylindrical bands or elements can also be manipulated in size to amplify views, zoom into data sets or images. As a user increases the height of a system cylindrical segment, as the available space to display data increases, so too does the fidelity of the data (e.g., cylindrical segment representing FiO2 with flags/markers can become a FiO2 vs. time graph as the cylindrical segment height increases).

A cylindrical band may display a plot or a graph of some data versus time. A clinician may want to increase the size of an interesting portion of the data to determine a more accurate picture patient data or vitals. Virtually touching or dragging the data or the cylinder over the data may expand the height and/or width of the cylinder and/or the corresponding data. In some implementations, as described further with regard to FIG. 14A, for data types which may be more easily viewed in a flat orientation (e.g. images, graphs, tables), one or more selected cylinders may unfold or unwrap into a more planar view. In some implementations, plots may be overlayed. The system may be configured to allow a clinician to perform a gesture or dragging motion in which one or more parameters are moved or dragged onto an area in the 3D space, and immediately appear as a new plot or graph. In some examples, new data may be dragged from multiple bands and co-plotted with multiple axes, if necessary, and a common time axis on the bottom.

The cylindrical bands may also be reordered by dragging or moving gestures. Two data sets may be combined by dragging one down data set displayed on a first band onto another second band and holding it there. Two cylindrical bands may also be combined by grabbing each of them with a finger and then pinching them together. The data may then be displayed together on the same band, for example, using a common time signature. Bands that include multiple data sets may be expanded or the data sets separated using a reverse pinch gesture. In some implementations, a secondary icon may float in the 3D space near the structure. The icon may include a symbol indicating the icon may be used to combine data. When a clinician drags one or more band towards the icon the system may combines the data with other data dragged to the icon, or create a new band with the data displayed on it.

Markers may also indicate start or end points. For example, for a patient being weaned off of ventilation, a marker may indicate the start of a sedation vacation or sedation awakening trial where the patient's sedation levels are reduced, or may indicate a spontaneous breathing trial where ventilator assistance is reduced to see if the patient may start to breath on his or her own. Markers may also indicate a point in time corresponding to when a patient missed a breathing trial, may indicate when a breathing trial was started late, the breathing trial wasn't coordinated with the sedation reduction, etc.

According to some implementations, the system may include machine learning algorithms to look for patterns in data and project what steps should be taken with regard to patient care. Markers may be automatically generated that correspond to future events or actions that should be performed. For example, if some event X has occurred in the past, then the machine may determine that Y will occur at a future time. Depending on the event, the machine may mark the future time point, signal a review of data at that specific future time point, and signal a likelihood of an event happening or signal an alert for a patient if the likelihood is a significant or morbid/undesirable event. In another example, machine learning may identify likely patient paths from a given pattern of data and, in some implementations, automatically make its own adjustments to care systems (e.g., as an autopilot). For example, on identifying a flow rate of ventilation is not providing a desired effect on the patient, the flow rate may be adjusted (e.g., within predetermined limits) to move the patient towards the desired effect. In some implementations, a caregiver may be provided an alert by the system. An example alert may be sent to a caregiver device, and include a text message indicating "heads up, your patient X is trending towards a ventilator-associated event" or "heads up, your patient Y is ready for weaning from ventilation."

If a user is observing the visual cylindrical health data element and sees a flag/marker/event on the ventilation/respiratory segment, the user can select that flag/marker/event. In order to provide a comprehensive picture of the patient's health including possible contributing factors in other systems, the cylindrical band/segment of choice (e.g., ventilation) may be rotated to bring the selected flag to the front of the cylindrical element closest to the user. At the same time, adjacent cylindrical segments related to other systems may automatically rotate and time align with that flag to provide a visual representation of what was happening with the patient in other systems at the same time point. As described further below with regard to FIG. 14B, as a band rotates and/or is being selected or interrogated for data or a marker, the front of the band may contain a band magnifier that enlarges a portion (e.g., the front piece) of the band for better viewing. In this regard, the band magnifier may both enlarge and time compress data.

Selection of screen elements is not limited to physical touch or key strokes on a keyboard or similar device but rather should be taken to encompass all possible selection methods including methods encompassed in virtual and augmented reality environments such as gesturing through eye movements or other body movements. The rotation of the visual cylindrical health data element enables a 360-degree view of the patient health condition and provides an immersive environment which through augmented reality and/or virtual reality may enable a user to explore more data in a centralized environment. For example, a tablet can be used with augmented reality to see significant amounts of patient data by enabling a user to walk around the visual health data cylinder and view it from all 360 degrees. Similarly, if wearing augmented reality glasses or virtual reality glasses (or similar imaging tools), one or more users can walk around the cylindrical health data element, gather around the element with other users or clinicians, and even spin and manipulate the cylinder in an interactive way to provide views to other users.

As depicted in FIGS. 1 through 5, the system may display an object representation of at least a portion of a human body. This object representation may be individualized for the patient based on the patient's profile and/or medical history. According to various aspects, the object representation may include a 3D human body and/or may include representations of various organs within the human body (e.g., lungs, heart, intestines, reproductive system according to the gender of the patient, etc.). For example, a human body representation may be displayed as male or female, or child or adult, be anatomically correct, and be generated based on demographic information, hair color, skin tone, weight, height, etc. According to various implementations, the representation may be displayed in the center of the cylindrical bands (e.g., along the axis of the bands) or may appear adjacent to the cylindrical bands. Portions of the 3D human body or the organs within the body may be illuminated to indicate relevance to a portion of data. In some implementations, portions of the body and/or organs within the body may be highlighted—and corresponding cylindrical bands of data generated—based on preexisting conditions determined from the patient's medical history or from events or conditions currently occurring with the body.

The system may display more than one human, for example, transplant patients, pregnant patients, and multiple data sets or overlapping data sets could be shared and viewed together when there is a commonality between more than one patient.

For example, flashing or illuminated lungs may indicate that the data includes one or more respiratory related markers. A relevant portion of the human body (e.g., lungs) may also illuminate or flash when data and/or a cylindrical band is selected that is representative of that portion of the human body (e.g., selecting ventilation data). In some implementations, the body may not stay as a fixed whole body. For example, the hollow outer body may disappear and the relevant portion of the human body (e.g., the lungs) may animate and grow in size to float in the 3D space in place of the outer body in response to certain events or actions, or selection of the related data. If the system detects a left lung injury or a lesion or a problem with something that's been placed inside the lung (e.g., from a lab or radiology report) the left lung may enlarge into the center of the view to highlight the detected issue. Selection of the radiology report or relevant data in the report, the lab, or on a cylindrical band may cause the corresponding portion of the human body to be expanded and/or highlighted.

Providing data on cylindrical bands surrounding portions of the human body relevant to that data provides the data in a more familiar environment. This way, the clinician doesn't have to think about how the data correlates to a particular issue. Additionally, the more data that is input and presented and manipulated, the more that machine learning can diagnose issues and predict future events. The system may automatically determine from a radiology report that there is an issue with the left lung and illuminate that portion of the lung. The clinician immediately sees the illuminated lung and knows to look for markers indicative of the issue. In some implementations, the degree of illumination (e.g., brightness, whether flashing, etc.) may be determined by the severity of the issue detected. The system (e.g., a rules engine) constantly interrogates markers and prioritizes issues that need to be looked at by a clinician. According to various aspects, this visual layer may operate with data that is coming in through an integration engine which is collecting data from individual devices, or through a hub connected to the individual devices. A knowledge layer, such as a rules engine and/or a machine-learning algorithm, may interrogate and/or analyze the data for markers, events, patterns, conditions, and the like. The system may automatically identify hot spots and bring up additional views or flag portions of the body in 3D in response to the prioritization. In some implementations, the system may also display textual messages to the clinician to alert them to markers. In some implementations, the system may generate an instruction or suggested action or provide a description of a marker or event for the clinician. Such textual messages may appear on or adjacent to the cylindrical band which is relevant to the marker or event.

Data drilling or interrogation can occur due to the depth of the core of the cylinder and similar to the functionality of the cylinder in being infinitely rotatable or vertically extended, the core of the cylinder on its side can be infinite or semi-infinite in that what is available is not limited to what is seen or what can be presented visually. The object representation can also serve as a source of indication related to health data or health condition. For example, if a flagged health data value exists for a patient, the centralized object representation can be flashing or can have an alternative method of alerting the clinician or user that there is an issue which should be attended to or acknowledged. When the user selects the displayed body, the visual cylindrical health data element can automatically display the system segment which contains the flag aligned to the front position and may additionally time-align other systems to provide a streamlined visual data path. The indication provided by the object representation may be specific to a body system (e.g., lungs flashing) or may be generalized to the entire body. The object representation element may be stationary or rotating or may have movement of another type which is visually helpful to expose the most comprehensive view of the patient condition.

In some implementations, the representation of the human body may also be used to indicate program operations. For example, when the system is actively collecting or acquiring data, the 3D body may rotate and, in some implementations, if the body is not rotating then no active data collection is going on.

Movement and visual presentation of cylindrical bands and elements can also be important to user interaction with the patient data—for example, cylindrical bands and elements can rise, fall, rotate, highlight, flash, or change orientation. For example, a cylindrical element can change from being viewed in perspective or vertically to being looked at on its end. In this way, patient health data can be presented or represented in different ways. For example, the core of the cylindrical space can be used to display a health data element or medical image while the circular bounds or outside of the circular bounds can be used to represent the time sequence of that type of health data as shown in FIG. 6 using X-rays as an example.

Figure 6:
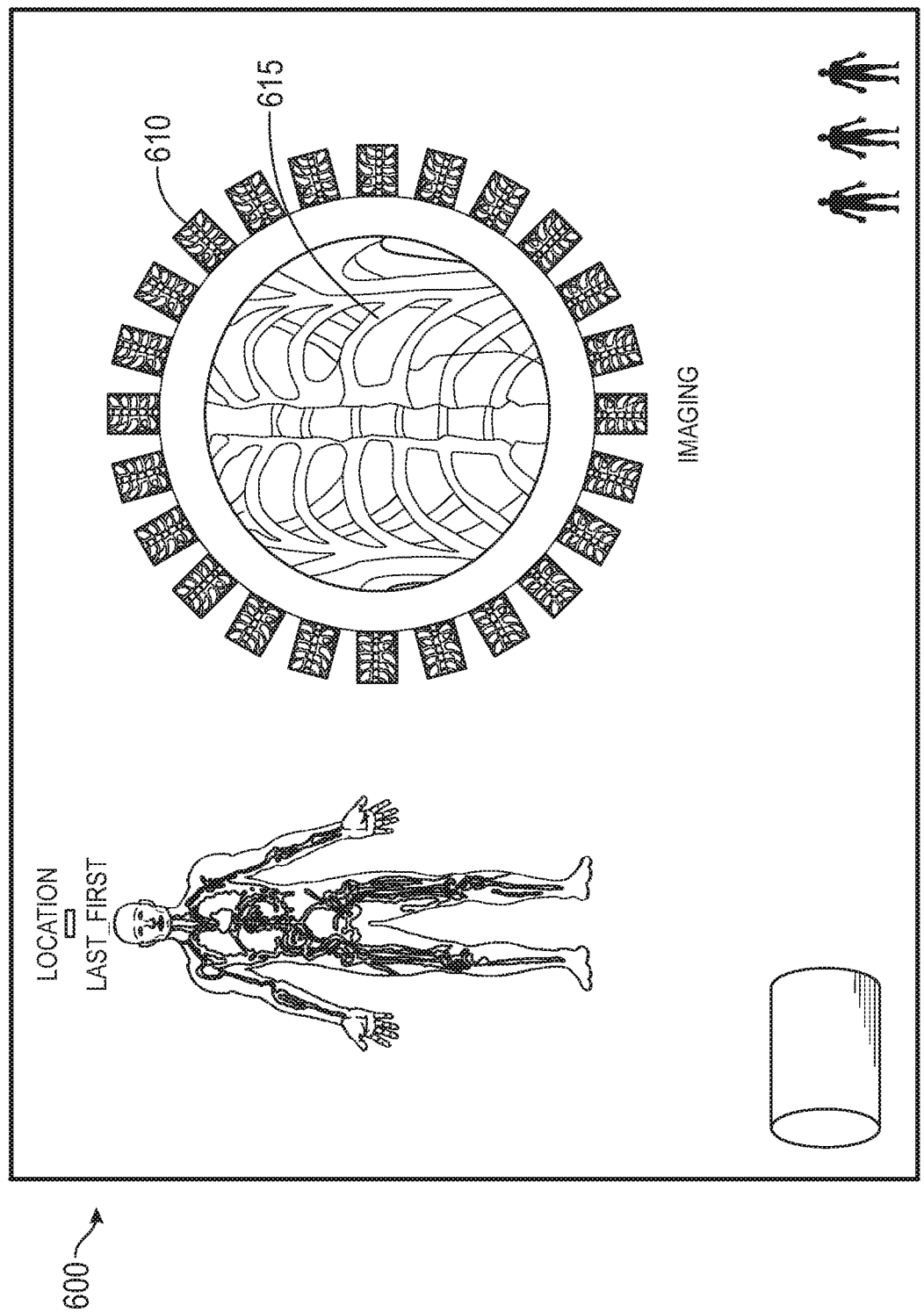
FIG. 6 depicts an example graphical interface, including a cylindrical data element surrounding a two dimensional image, the data element functioning as an image selector and displayer with rotational time, according to various aspects of the subject technology.

FIG. 6 depicts an example graphical interface 600, including a cylindrical data element 610 surrounding a two-dimensional image area 615, with the data element 610 functioning as an image selector and displayer with rotational time, according to various aspects of the subject technology. Some fixed data (e.g., radiology images or a lab report) may be represented on a cylindrical element and not include a time parameter. For example, data displayed on a cylindrical element may be marked with a radiology or imaging marker. In such cases, selecting the marker corresponding to the data may cause the display of a different type of a visual that's larger and conducive to reading. A new dialog 610, 615 may appear in the 3D space as a floating 2D plane. The 2D plane may be positioned with respect to the same axis as the cylindrical band(s) such as to be able to be rotated for display to other clinicians in an augmented reality space. In the depicted example, the dialog is an image viewing dialog that has access to multiple images (e.g., x-rays) and includes a rotatable data element 610, which is rotatable about an image area 615, for selection of one of the multiple images to display in image area 615. In the depicted example, multiple x-ray images are displayed about the image area 615 for selection, and a selected x-ray image is displayed in image area 615. The graphical interface in FIG. 6 may be included in a given virtual reality interface as described above in FIGS. 1-5.

Figure 7:
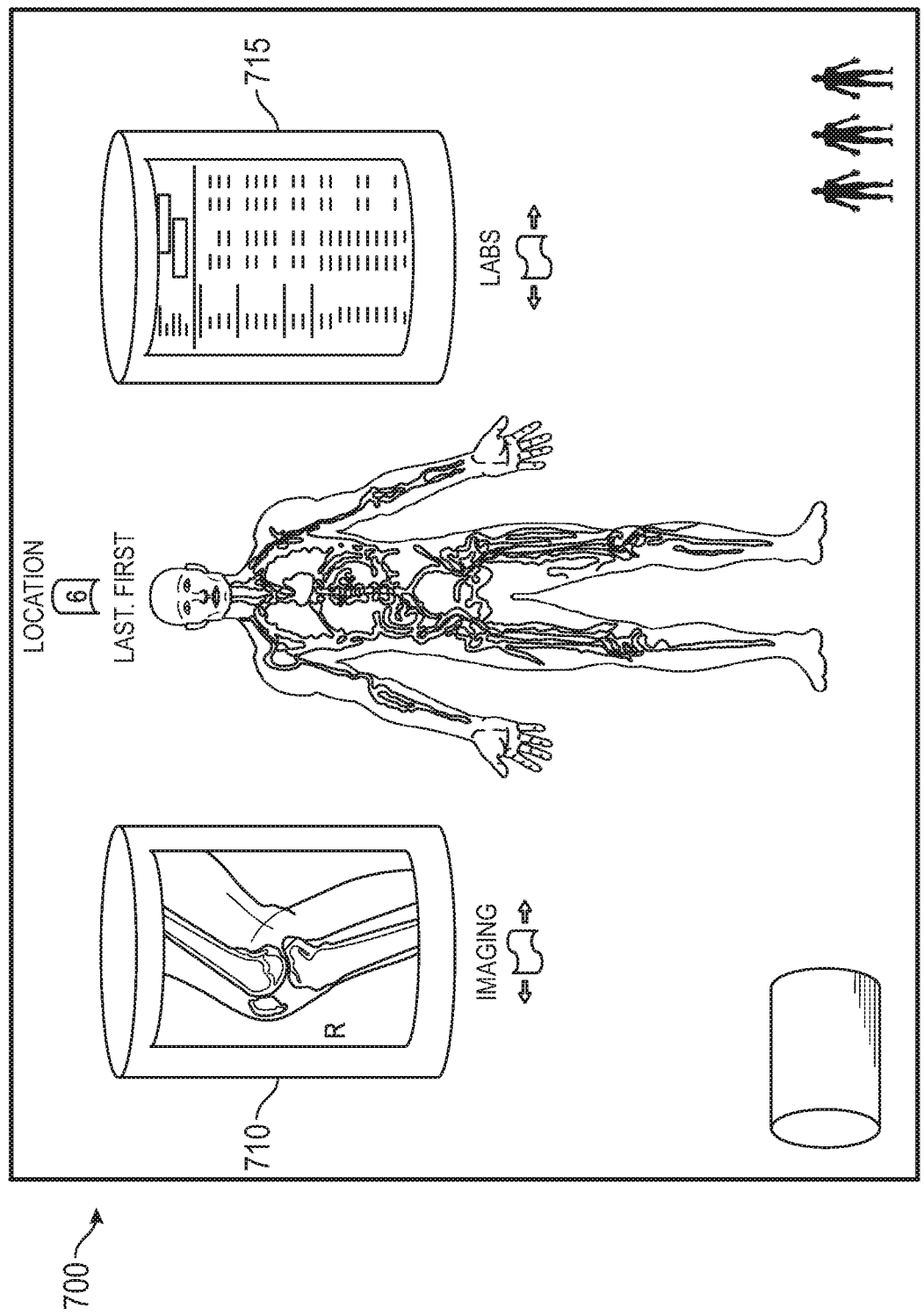
FIG. 7 depicts an example graphical interface, including cylindrical structures for displaying labs, vitals, and images, according to various aspects of the subject technology.

The core of the interaction with the patient population and individual patient according to this disclosure may be achieved entirely or substantially through cylindrical elements. For example, cylindrical elements or cylindrical element orientations other than the cylindrical band structure examples shown in FIGS. 1 through 5 can be utilized for control functions and display functions. For example, when viewing laboratory slips or vital signs or tabular data or images, it may be undesirable to view such items on an elongated horizontal form such as that shown in FIGS. 1 through 5. In this case, virtual cylinders with smaller aspect ratios can appear or pop out of the centralized data cylinder. These smaller virtual cylinders may be more conducive to viewing these items. FIG. 7 depicts an example graphical interface 700 including a first cylindrical structure 710 that functions as a first image viewing dialog to display images such as an x-ray of the patient, and a second cylindrical structure 715 that functions as a second viewing dialog to display patient labs and/or vitals (e.g., in image and/or textual form). These cylindrical structures 710, 715 are separate from the centralized virtual cylinder structure depicted in FIGS. 1 through 5, and may be depicted alone or together with the centralized virtual cylinder structure.

With further reference to FIGS. 6 and 7, the foregoing image viewing dialogs may be configured to display images associated with a patient. In some implementations, an image viewing dialog may include an image viewing area displaying the first image, and circumscribed by multiple icons representative of selectors for other images to display in the image viewing area. In response to receiving an icon selection of one of these icons, the dialog may be configured (e.g., by instructions) to display a second image (corresponding to the selection) in the viewing area.

Figure 8:
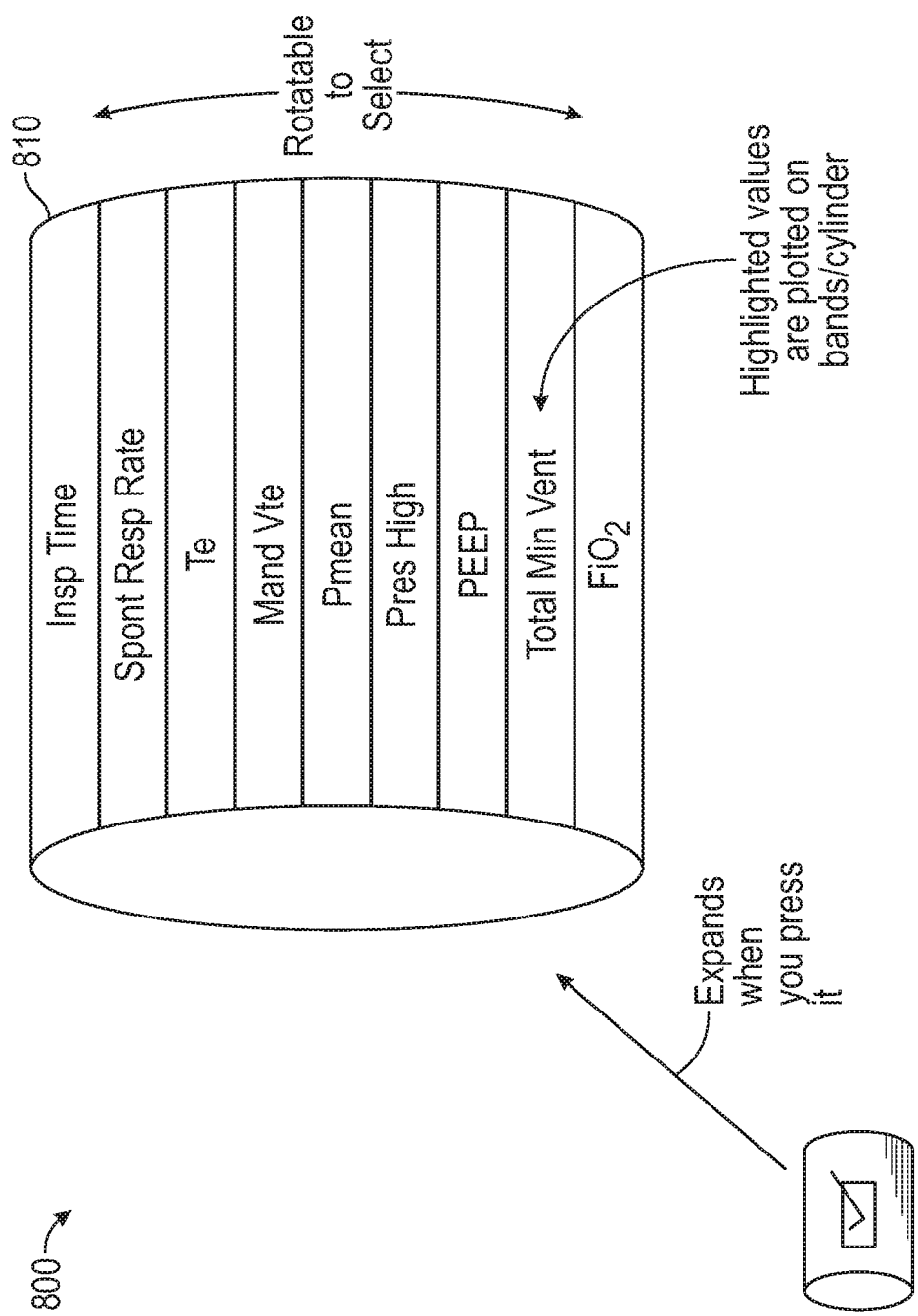
FIG. 8 depicts an example graphical interface, including a cylindrical selection wheel for display metrics/data streams, according to various aspects of the subject technology.

FIG. 8 depicts an example graphical interface 800, including a cylindrical selection wheel 810 for display metrics/data streams, according to various aspects of the subject technology. According to various implementations, a selection icon 805 may be provided on virtual reality interface 100 for the selection of various items, including between available data sets. When selected, the selection icon 805 may expand into the depicted cylindrical selection wheel 810. Selection wheel 810 is rotatable in a vertical direction to select between the various data sets. In one example, a predetermined gesture with respect to a cylindrical element may cause virtual reality interface 100 to briefly display selection icon 805, which may then be activated to use selection wheel 810 to change the data displayed in the cylindrical element. In another example, the selection icon 805 and corresponding cylindrical selection wheel 810 may be used to select values to display in virtual listing 150. While cylindrical selection wheel 801 is depicted as moving in a horizontal direction for selections, cylindrical selection wheel 810 may move in a horizontal direction to perform the same selections.

Figure 9A:
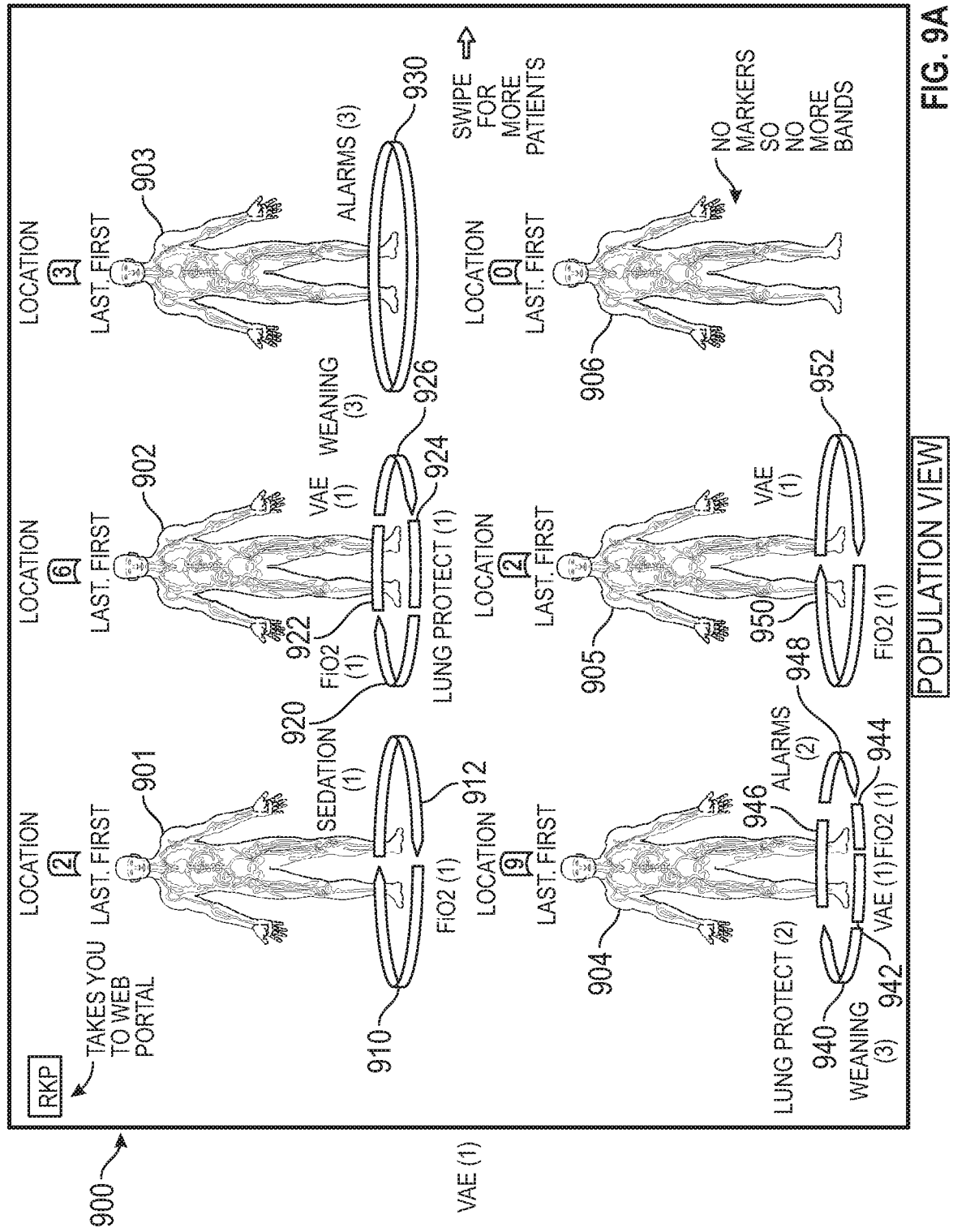
FIGS. 9A and 9B depict examples of a virtual reality interface, including a patient population view of multiple patient representations, each with cylindrical bands displaying example markers, according to various aspects of the subject technology.

FIG. 9A depicts a first example of a virtual reality interface 900, including a patient population view of multiple patient representations, each with cylindrical bands displaying example markers, according to various aspects of the subject technology. As illustrated in FIG. 9A, the patient population view includes a graphical representation of a care area patient population, including patient 901, patient 902, patient 903, patient 904, patient 905, and patient 906. As further illustrated, cylindrical bands 910 and 912 are provided for the patient 901. Cylindrical bands 920, 922, 924, and 926 are provided for the patient 902. Cylindrical band 930 is provided for the patient 903. Cylindrical bands 940, 942, 944, 946, and 948 are provided for the patient 904. Further, cylindrical bands 950 and 952 are provided for the patient 905.

The cylindrical band elements around each patient shown in the population view of FIG. 9A are visual representations of patient markers/flags/events relevant to the patient's respiratory and sedation medication status. In particular, a cylindrical band element around each patient is segmented according to markers in each of six categories which include FiO2 (fraction of inspired oxygen), sedation, weaning, lung protection, alarms compliance, and ventilator-associated events (VAEs). In each segment where at least one marker exists, the number of markers is displayed. Above each patient, the total number of markers is also displayed such that with a quick view, a clinician can determine both the overall status of their patient population as well as the status of any given patient. Segmentation of the cylindrical band is controlled by the number of categories with markers such that if a patient has no markers, no cylindrical band may be displayed. Touching or gesturing or selecting a patient by other possible means (e.g., AR or VR selection) in the Population View takes the clinician/user to an Individual View (FIG. 10).

Figure 9B:
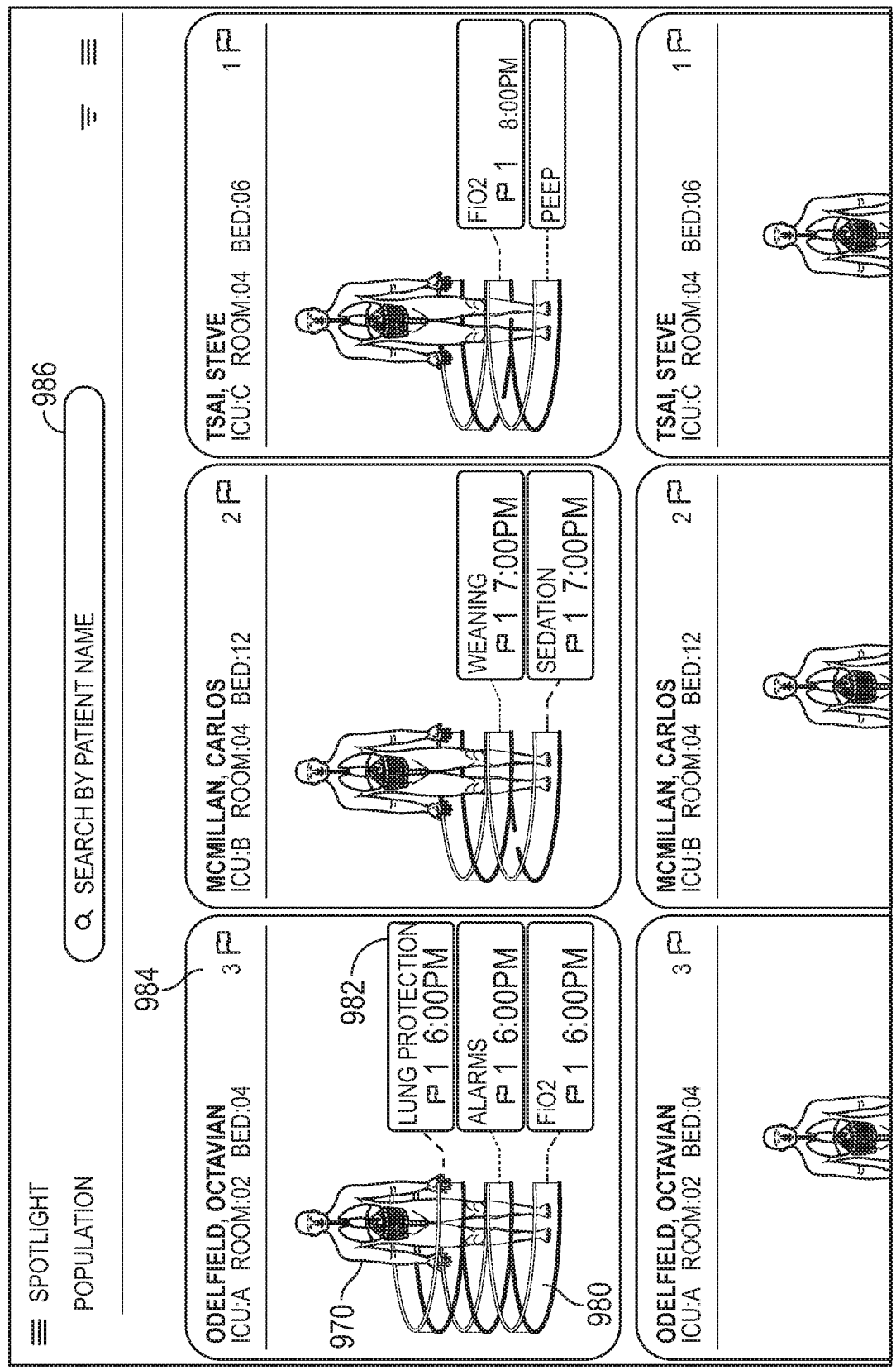

FIG. 9B depicts a second example of a virtual reality interface 900, including a patient population view of multiple patients representations 970, each with cylindrical bands displaying example markers, according to various aspects of the subject technology. In this example, each patient representation 970 may be at least partially surrounded by one or more bands 980, with each band indicating a category of data. In some implementations, bands may display in interface 900 responsive to a marker being generated, for example, by predetermined threshold being satisfied. In this regard, a marker may also represent an alarm condition. A graphical marker label 982 may be visually associated with each band (e.g., by way of a color coordinated lead or arrow), and may display the number of markers and/or alarms corresponding to the data category of each band, and a time that each marker or alarm condition was triggered. A visual marker designation 984 may also be displayed within interface 900 for each patient, each indicating the total number of markers that are active and/or visually indicated in the interface for the corresponding patient. Where there are more patients than can be displayed on a single screen, interface 900 may include a search input 986 by which a patient name, identifier, or partial name or identifier, may be entered to initiate a search and display of a patient population view of patients matching the search results.

The example care area patient population interfaces of FIGS. 9A and 9B may also include aspects of the depicted cylindrical elements but viewed from above rather than in a perspective or front view. For example, in one implementation, a collection of patients is viewed from above, for example, looking down upon the top of their heads. Around each patient representation is a circular or cylindrical element which provides indications of flagged or marked values or conditions. The color of the cylindrical element may indicate the status of a system or monitor or flag. Alternatively, the color of the patient representation may provide this indication. Furthermore, information relevant to markers or flags or important health information may be presented around the patient within the cylindrical or circular element space. If a patient within this population is selected by means of touch or other means by the user, a representation of the patient and/or associated markers or flags may rise out of the population into the individual cylindrical health data element described above (e.g., in FIGS. 1 through 5). In this way, the cylindrical health data element is maintained within different views structures which provide either the same or different information, however, the structure of the patient population view provides the user with a global image of a patient population of interest.

Figure 10:
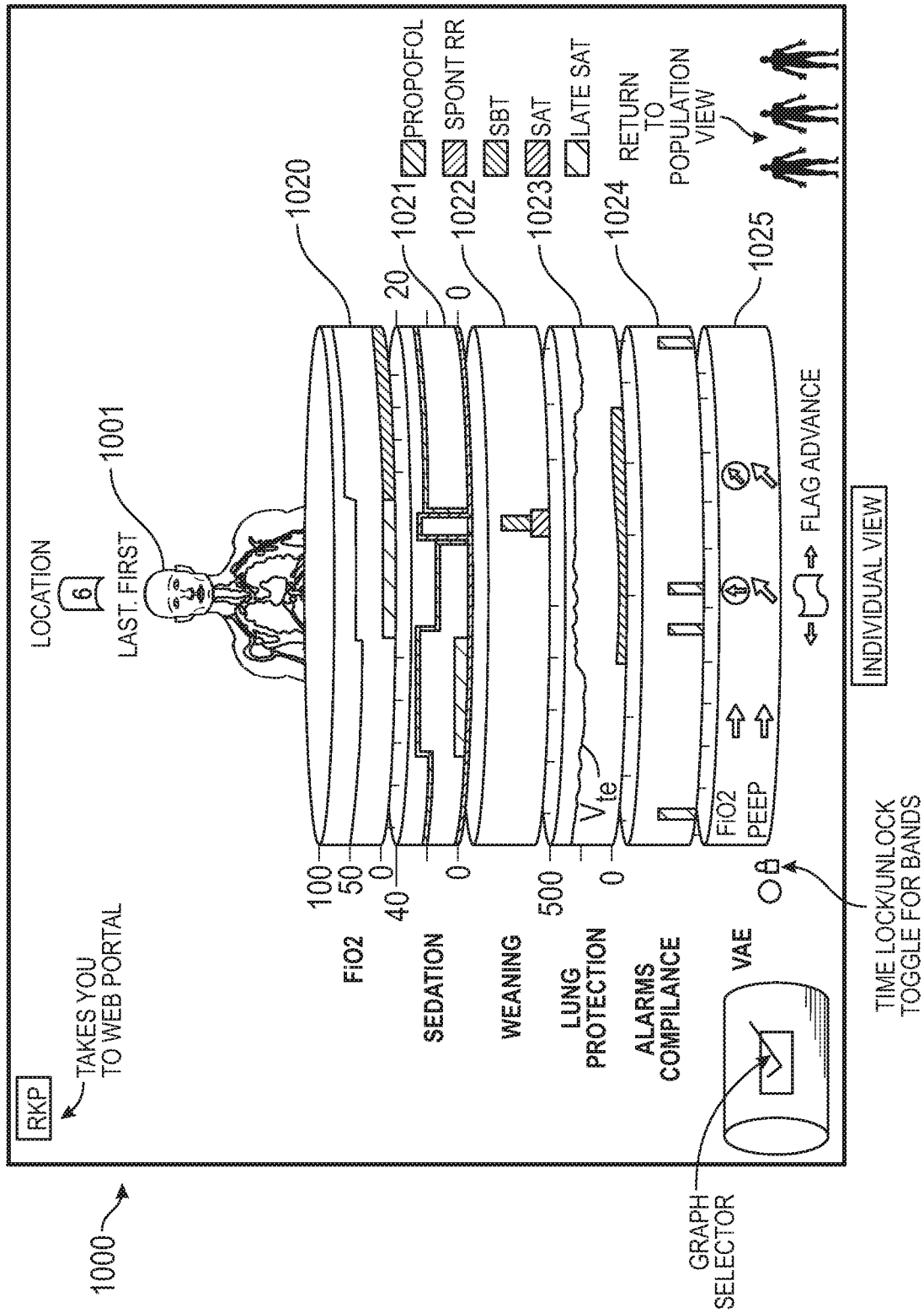
FIG. 10 depicts an example virtual reality interface, including an individual patient view with cylindrical bands displaying respiration and sedation markers, alarms compliance, time-series data, and protocol adherence, according to various aspects of the subject technology.

FIG. 10 depicts an example virtual reality interface 1000, including an individual patient view with cylindrical bands displaying respiration and sedation markers, alarms compliance, time-series data, and protocol adherence, according to various aspects of the subject technology. As illustrated, a visual cylindrical data element 1020, visual cylindrical data element 1021, visual cylindrical data element 1022, visual cylindrical data element 1023, visual cylindrical data element 1024, and visual cylindrical data element 1025 are included in the virtual reality interface 1000. Each of the visual cylindrical data elements respectively provides a visual representation a data stream of physiological data associated with a patient 1001.

FIG. 10 contains an implementation of an Individual View in the subject technology. The Individual View consists of a cylindrical health data element which is structured as six cylindrical bands which represent the six aforementioned marker categories. On each cylindrical band, discrete markers/flags or events are displayed along a timeline, or a continuous data value (e.g., FiO2 or tidal volume) is presented as a time series, or both of these data types can be displayed simultaneously. The cylindrical bands can be manipulated/rotated freely using gesturing or can be advanced forward or backward using a flag advance button. A time-alignment lock provides a mechanism to toggle between having all cylinders rotate together in a time-aligned fashion or having individual cylinders rotate independently. A second set of cylindrical bands is contained below the level where the patient representation is standing (i.e., under the floor). Using a swiping gesture, this second set of six cylindrical bands can be switched with the marker related bands. A user can select data sources or elements to present on each of these six bands using a cylindrical graphing element selection wheel similar to that shown in FIG. 8. A user may return to the population view at any time using a population-view button in the view.

According to some implementations, visual cylindrical elements can also be joined or interlocked like gears such that moving a visual cylinder in one plane advances or rotates a connected visual cylinder in another plane. Similarly, small cylinders can be used to advance larger cylinders within the same plane. In this way a cylindrical control can be used to advance a larger element. Furthermore, 'gearing' ratios can be used to manipulate the cylinders of the subject technology, either directly or through associated connected cylinders. For example, when using a gesture to rotate a cylinder which contains a very large amount of compact data or large number of flags or markers, said gesture can be scaled such that each real unit of motion in gesturing translate to ¹⁄₁₀th or 1/xth of said gesture on the cylindrical band or element. Additionally, to improve viewing of data or data graphs, as the user rotates a given data set or trend to the front of the cylinder, that region of the cylindrical band can automatically enlarge for improved viewing.

Variants of the idea or invention comprise alternative ways to structure the cylinders or interaction of the cylinder with the user, the structure of the displayed object representation. It should be noted that the object representation aspect of the visual element is tailored to the patient of interest, i.e., if the actual patient is a neonatal patient, so too may be the object representation.

The cylindrical health data element enables the visual presentation of data and markers/flags from separate systems in a consolidated, compact cylindrical structure or set of cylindrical structures with time-alignment of flags and markers which provides time-based visual data patient or clinical insights. Population-based data and patient views are provided in a cohesive three-dimensional visual structure which makes it possible to view patient data in a simplified visual rather than in the traditional formats of numeric tables, dashboards, data array and lists. This disclosure enables combining of data from a variety of sources to calculate data that is otherwise not available in a single structure. Adjustability of cylinder height and rotation enables unique visual interaction with both data and other clinicians who may be viewing the same cylindrical structure from other perspectives or locations. Visual temporal alignment of markers and flags from different hospital and diagnostic systems in a consolidated graphical structure (health data cylinder) provides visual consolidation of events and timelines necessary to produce patient data insights not possible in traditional or current art visual representations.

Figure 11:
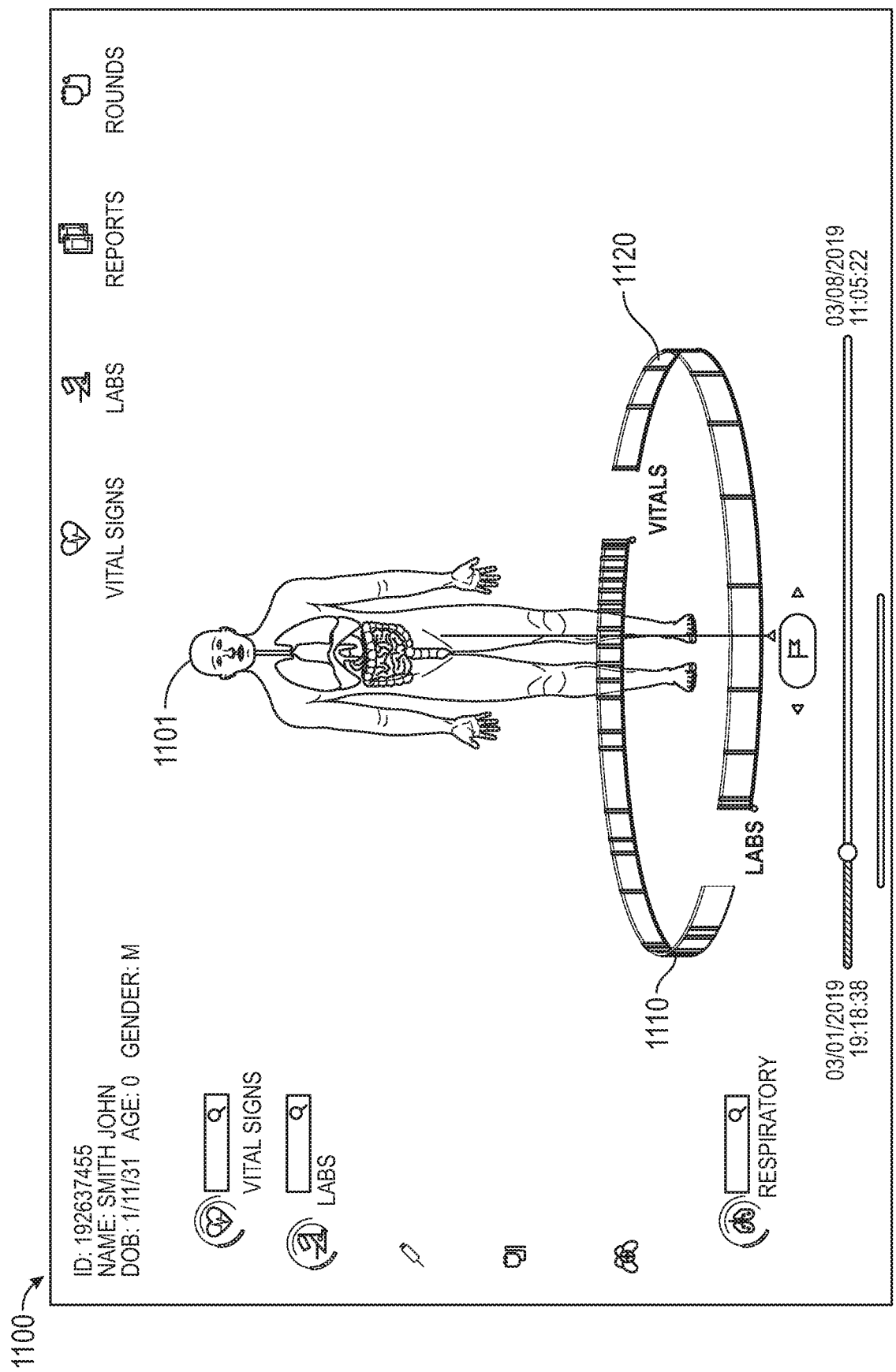
FIG. 11 depicts a further example virtual reality interface, including cylindrical bands with data flags/markers, according to various aspects of the subject technology.

FIG. 11 depicts a further example virtual reality interface 1100, including cylindrical bands with data flags/markers, according to various aspects of the subject technology. In some implementations, the 3D perspective of structures within an interface may be changed (e.g., by a click and drag operation, touch gesture, or the like). As illustrated in FIG. 11, the virtual reality interface 1100 includes a graphical representation of a patient 1101, with cylindrical bands 1110 and 1120, rotated such that the angle of viewing is from a perspective below the patient 1101.

Figure 12A:
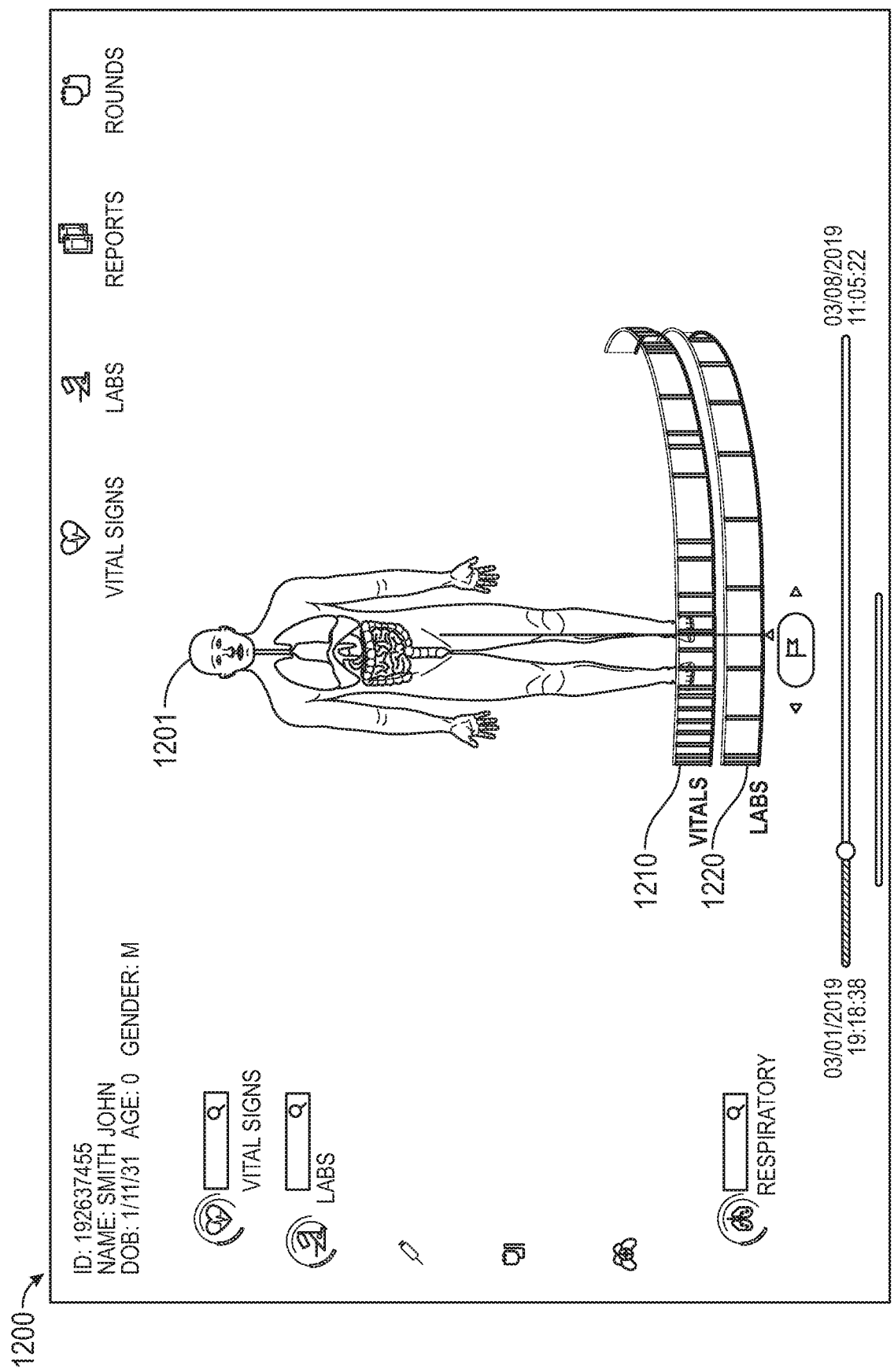
FIGS. 12A, 12B, and 12C depict further examples of virtual reality interface, including cylindrical bands with data flags/markers, according to various aspects of the subject technology.
Figure 12B:
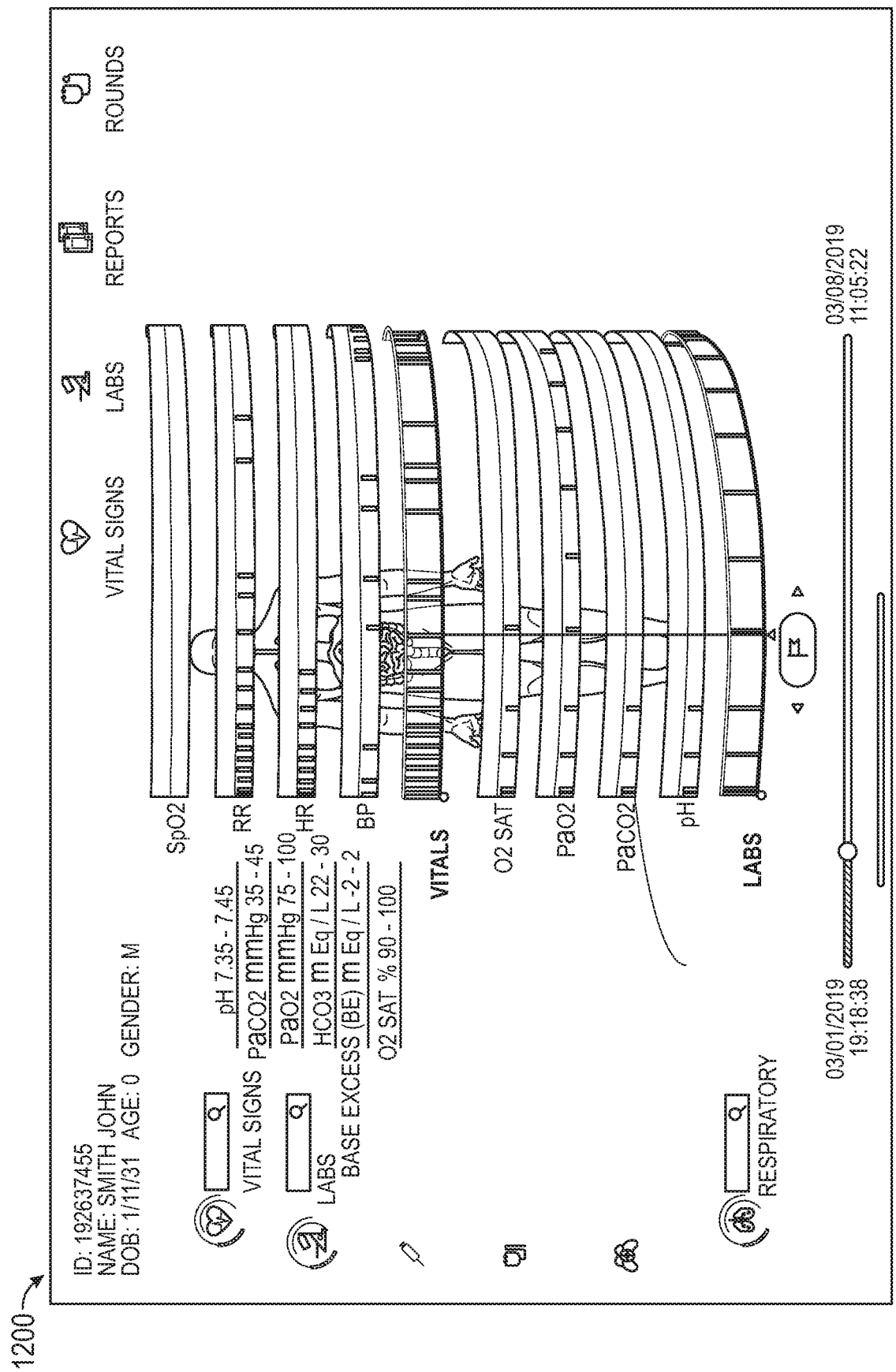
Figure 12C:
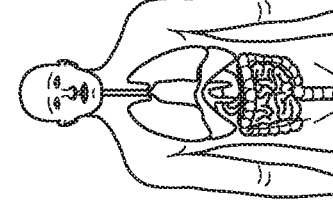

FIGS. 12A, 12B, and 12C depict further examples of virtual reality interface 1200, including cylindrical bands with data flags/markers, according to various aspects of the subject technology. As illustrated in FIG. 12A, the virtual reality interface 1200 includes a graphical representation of a patient 1201. As further illustrated, cylindrical bands 1210 and 1220 are illustrated for the patient 1201.

Figure 13A:
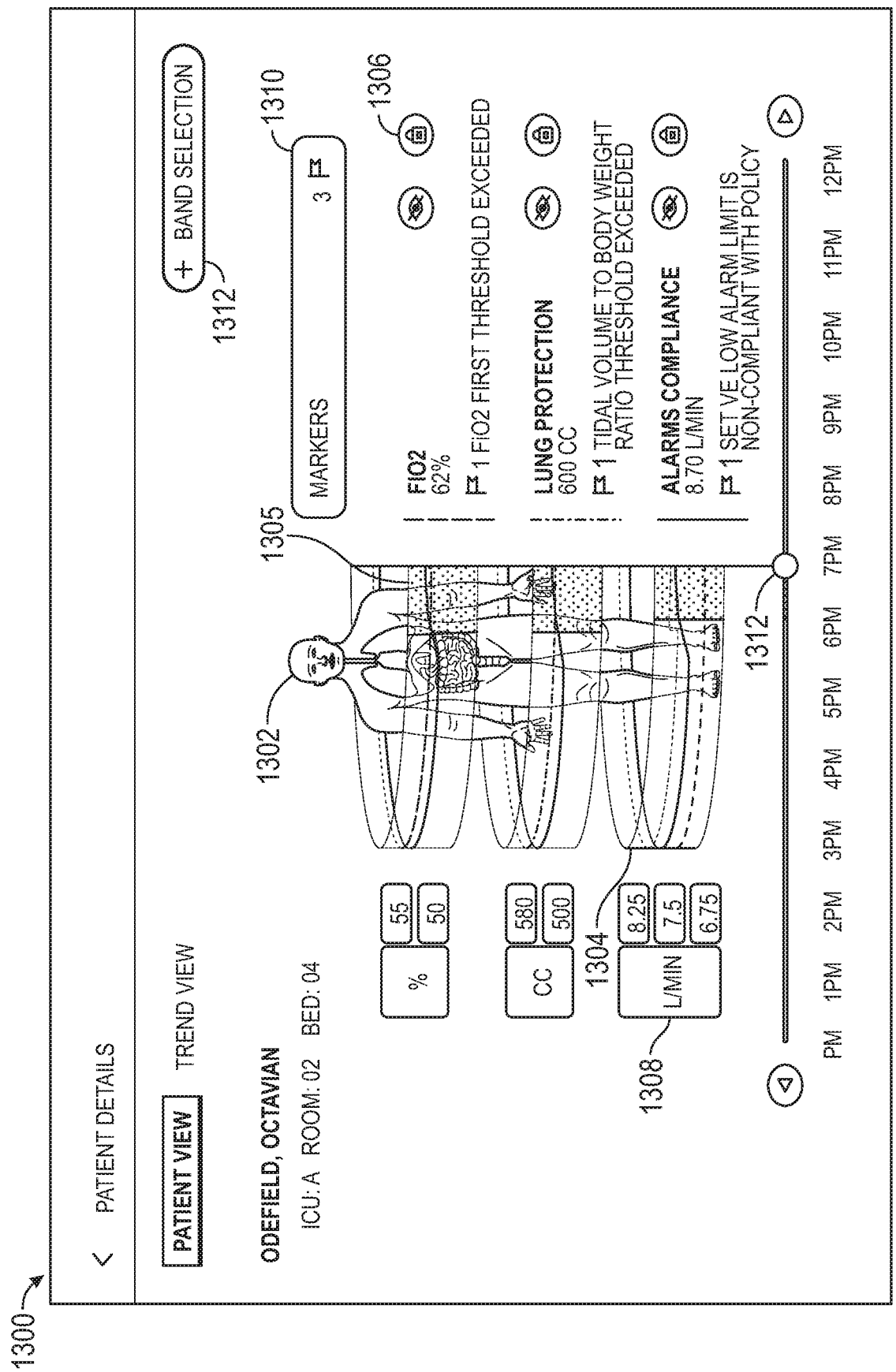
FIGS. 13A and 13B depict examples of a virtual reality interface, including a patient representation with one or more cylindrical bands displaying example data and markers, according to various aspects of the subject technology.
Figure 13B:
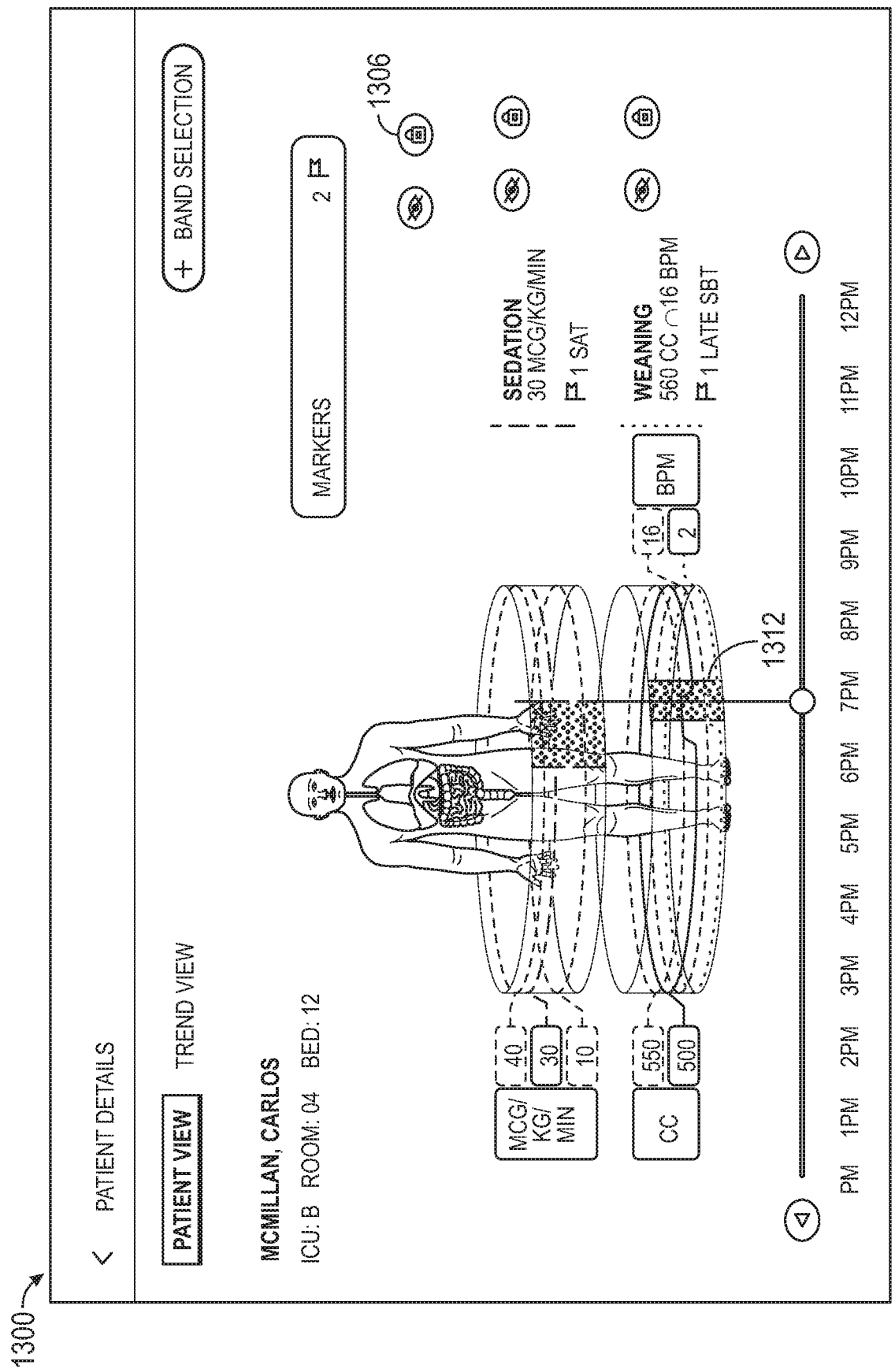

FIGS. 13A and 13B depict examples of a virtual reality interface 1300, including a patient representation with one or more cylindrical bands displaying example data and markers, according to various aspects of the subject technology. In this example, patient representation 1302 may be at least partially surrounded by one or more bands 1304, with each band indicating a category of data. In some implementations, the bands may display in interface 1300 responsive to a marker 1305 being generated for a corresponding category of data, for example, when a predetermined threshold being satisfied. In this regard, a marker 1305 may also represent an alarm condition. According to various implementations, a marker 1305 may be visually represented in the cylindrical band as a shaded portion corresponding to a portion of the data for which the marker is associated. For example, a marker 1305 may start at a position on the band corresponding to when the data satisfied (e.g., surpassed) a predetermined limit, and end at a position corresponding to when the data returned to a stable value (e.g., within the limit) or at a position corresponding to a current value of the data, for example, when the limit remains satisfied.

According to various implementations, a graphical marker label 1306 may be visually associated with each band (e.g., by way of a color coordinated lead or arrow), and may display the number of markers and/or alarms corresponding to the data category of each band, and a time that each marker or alarm condition was triggered. Label 1306 may also display a textual description for the marker or alarm. As depicted, label 1306 may also display a title of the data category (e.g., FiO2, Lung Protection, Alarm Compliance, etc.) and a current value of the data (e.g., percentage value, dosage (in CC), or rate (e.g., L/min), etc.). Similarly each band may also be associated with a graphical limit indicator 1308 indicating one or more predetermined limits on the data displayed by the corresponding band (e.g., upper and/or lower limits), and a current and/or averaged or mean value of the data displayed for a period of time. A visual marker designation 1310 may also be displayed within interface 1300 for the patient 1302, indicating the total number of markers that are active and/or visually displayed for the patient. According to various implementations, interface 1300 may also include a band selector icon 1312 for selecting data categories to be displayed within bands in interface 1300. When activated, band selector 1312 may cause the display of a listing of available data categories, which may be selected by way of a touch or gesture or similar user selection method. As described previously, virtual interface 1300 may include a graphical slider 1312 which, when activated in a direction (e.g., slid horizontally to the left or right), will rotate the displayed cylinders according to the direction the graphical slider 1312 is moved. In the depicted example of FIG. 13A, the cylinders selected for rotation may move within the partial circular path displayed, for example, within the bounds of a quarter circle terminating at first and second edges in the 3D space.

Figure 14A:
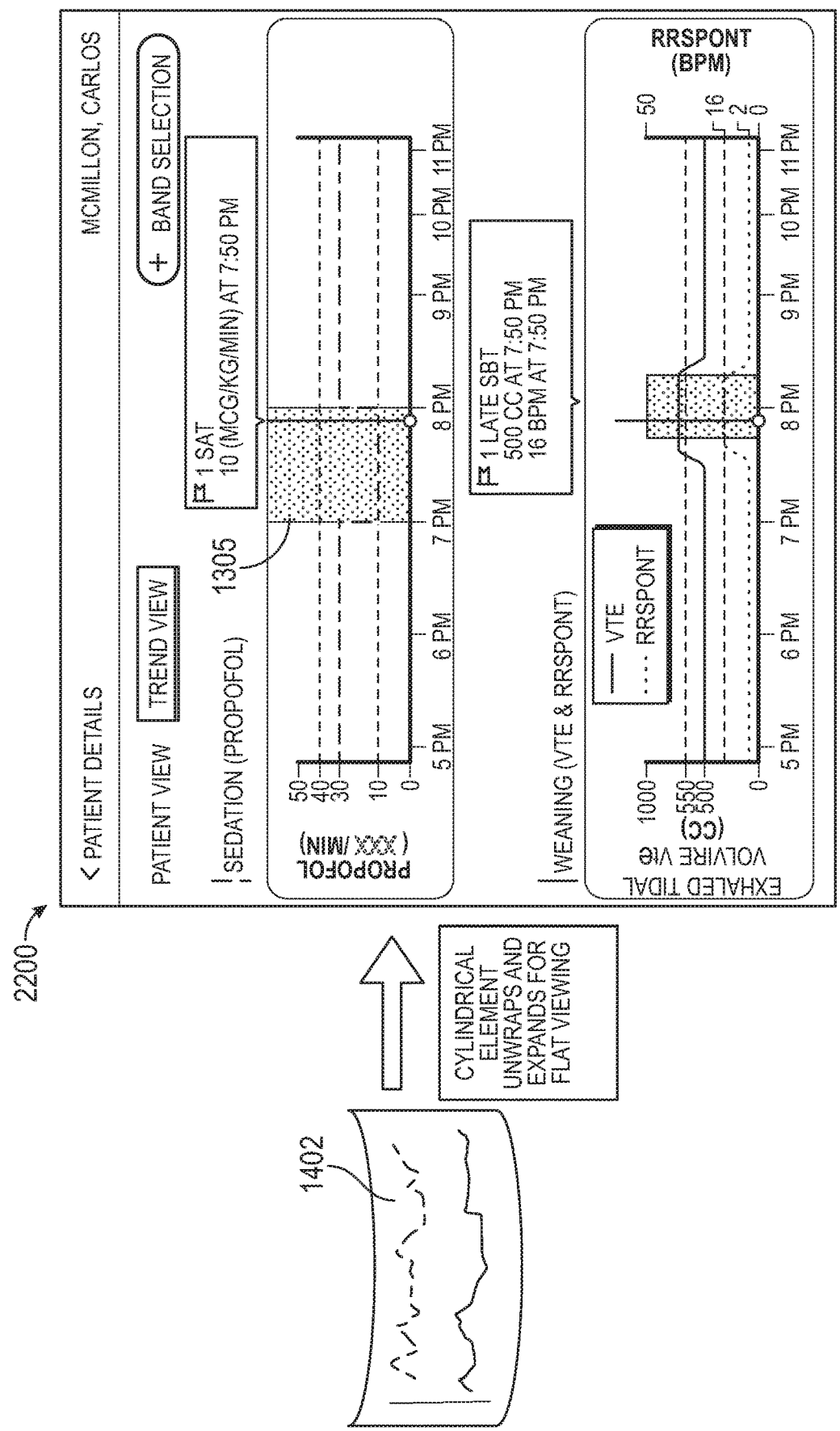
FIGS. 14A and 14B depict example alternative views of a cylindrical band, according to various aspects of the subject technology.

FIG. 14A depicts a first example alternative view of a cylindrical band, including a data marker displayed on the band, according to various aspects of the subject technology. In some implementations, cylinders may unfold or partially unfold/unwrap to form flatter viewing surfaces. A cylindrical band 1402 may be selected to display the data of the band in an exploded, flat view of the data. On selection, the data may be redisplayed in a two-dimensional interface 1400, and enlarged to display various aspects of the data values, including a current value of the data and corresponding limits on the data. For example, the visualization becomes unwrapped, similar to cutting a can or cylinder vertically and then unwrapping it into a flat or flatter view. Accordingly, data types that are more appropriately viewed in a flat rather than curved view may be enhanced, while preserving the cylinder structure in the 3D display. Markers 1305 may also displayed, as described previously.

Figure 14B:
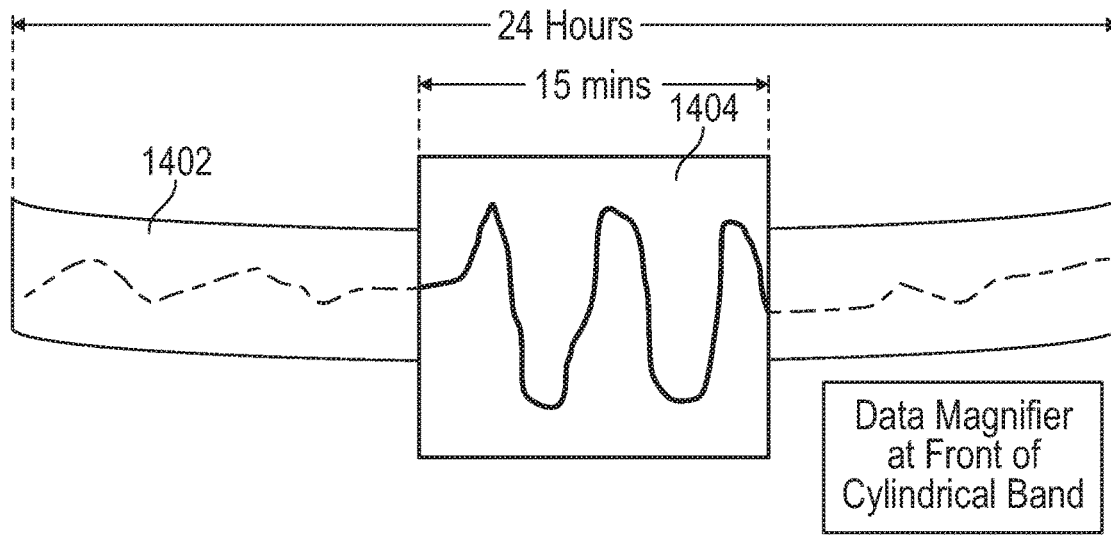

FIG. 14B depicts a second alternative view of a cylindrical band with a portion of the band magnified, according to various aspects of the subject technology. In some implementations, as a band 1402 rotates and/or is being selected or interrogated for data or a marker, the band may be displayed together with a band magnifier 1404 that enlarges a portion (e.g., the front piece) of the band for better viewing. The band magnifier 1404 may be activated for display in response to, for example, a predetermined gesture, or by way of activating a predetermined hardware button on either a pointing device or keyboard. The band magnifier 1404 is depicted as a box (e.g., in a shape similar to a belt buckle), but may alternatively be depicted as a circle or other shape. As illustrated in the depicted example, the band magnifier 1404 may enlarge and/or time compress data for a period of time. The band magnifier may, for example, show a blown up view of a predetermined period of time (e.g., 15 minutes) surrounding an event, even if the rest of the band is on a larger time scale (e.g., 24 hours).

Figure 15:
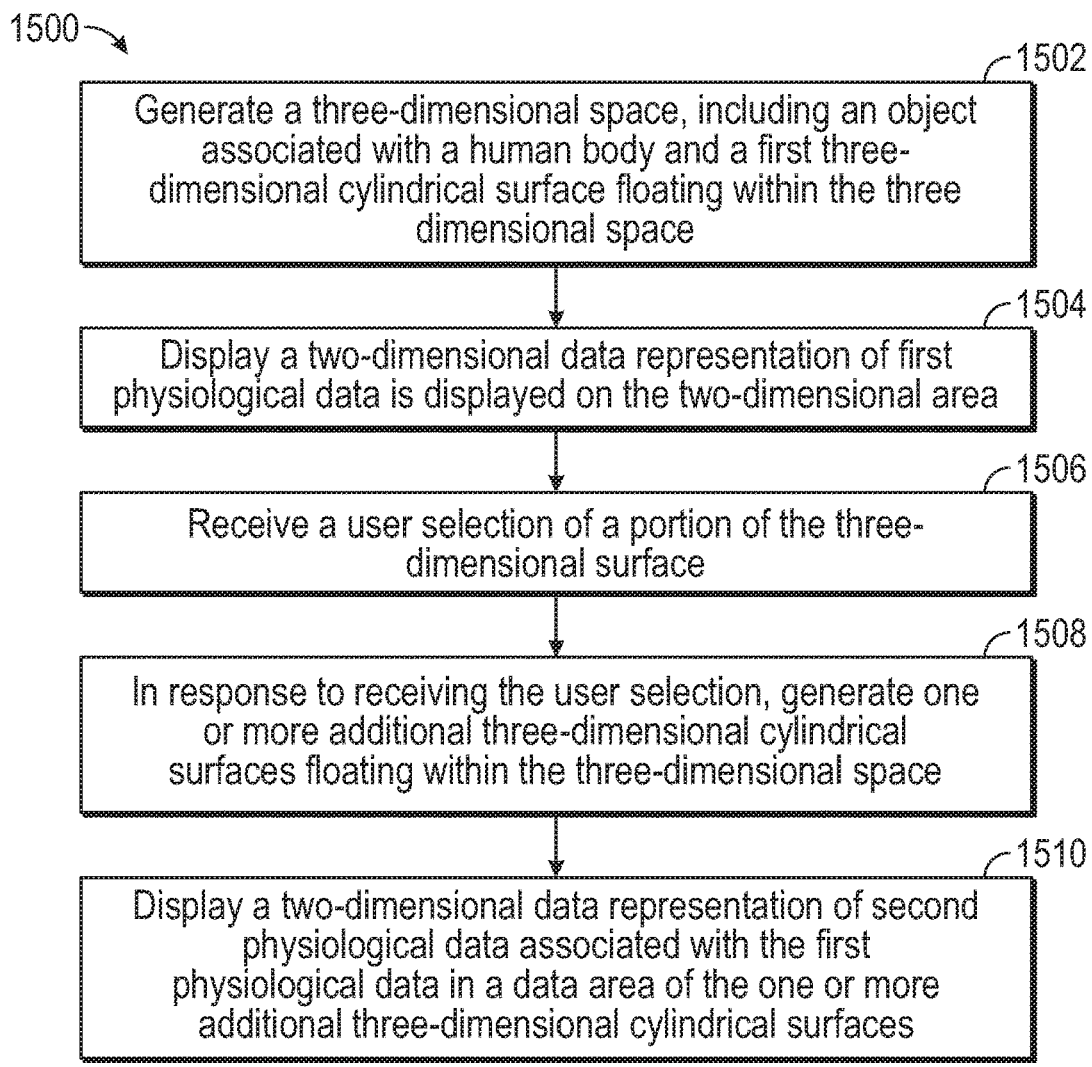
FIG. 15 depicts an example process for generating a virtual reality interface for the display of patient health data, according to various aspects of the subject technology.

FIG. 15 depicts an example process for generating a virtual reality interface for the display of patient health data, according to aspects of the subject technology. For explanatory purposes, the various blocks of example process 1500 are described herein with reference to FIGS. 1-14, and the components and/or processes described herein. The one or more of the blocks of process 1500 may be implemented, for example, by a computing device, including a processor and other components utilized by the device. In some implementations, one or more of the blocks may be implemented apart from other blocks, and by one or more different processors or devices. Further for explanatory purposes, the blocks of example process 1500 are described as occurring in serial, or linearly. However, multiple blocks of example process 1500 may occur in parallel. In addition, the blocks of example process 1500 need not be performed in the order shown and/or one or more of the blocks of example process 1500 need not be performed.

In the depicted example flow diagram, a three dimensional space is generated, including an object associated with a human body and a first three-dimensional cylindrical surface floating within the three dimensional space (1502). According to various implementations, the three-dimensional cylindrical surface has a height dimension and a length dimension circumscribed about at least a portion of the object, the height and length together defining a two-dimensional data area for the presentation of data to a user viewing the three-dimensional cylindrical surface in the three-dimensional space.

Concurrently with generating the first three-dimensional cylindrical surface, or shortly thereafter, displaying a two-dimensional data representation of first physiological data is displayed on the two-dimensional area (1504). The first physiological data may include one or more events associated with the first physiological data. For example, as depicted in FIG. 1, the first physiological data may include events that correspond to data satisfying or exceeding a predetermined threshold (e.g., an FiO2 level being out of bounds). A user selection of a portion of the three-dimensional surface is received (1506). The portion of the three-dimensional surface selected may directly correspond to an event displayed on the two-dimensional area. In response to receiving the user selection, one or more additional three-dimensional cylindrical surfaces is generated, floating within the three-dimensional space (1508). According to various examples, the additional three-dimensional cylindrical surfaces are displayed above or below and adjacent to the first three-dimensional cylindrical surface, each additional three-dimensional cylindrical surface being circumscribed about the portion of the object. Concurrently with generating the one or more additional three-dimensional cylindrical surfaces, or shortly thereafter, a two-dimensional data representation of second physiological data associated with the first physiological data is displayed on a data area of the one or more additional three-dimensional cylindrical surfaces (1510).

The first and/or second physiological data may be real time data associated with a patient. For example, a data stream corresponding to a physiological parameter of a patient may be received. The two-dimensional data representation of the first and/or second physiological data may be a visualization of at least a portion of the data stream. In one or more implementations, the first physiological data may be events that correspond to thresholds being met in the second physiological data (or vice versa).

Many aspects of the above-described example 1500, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 16:
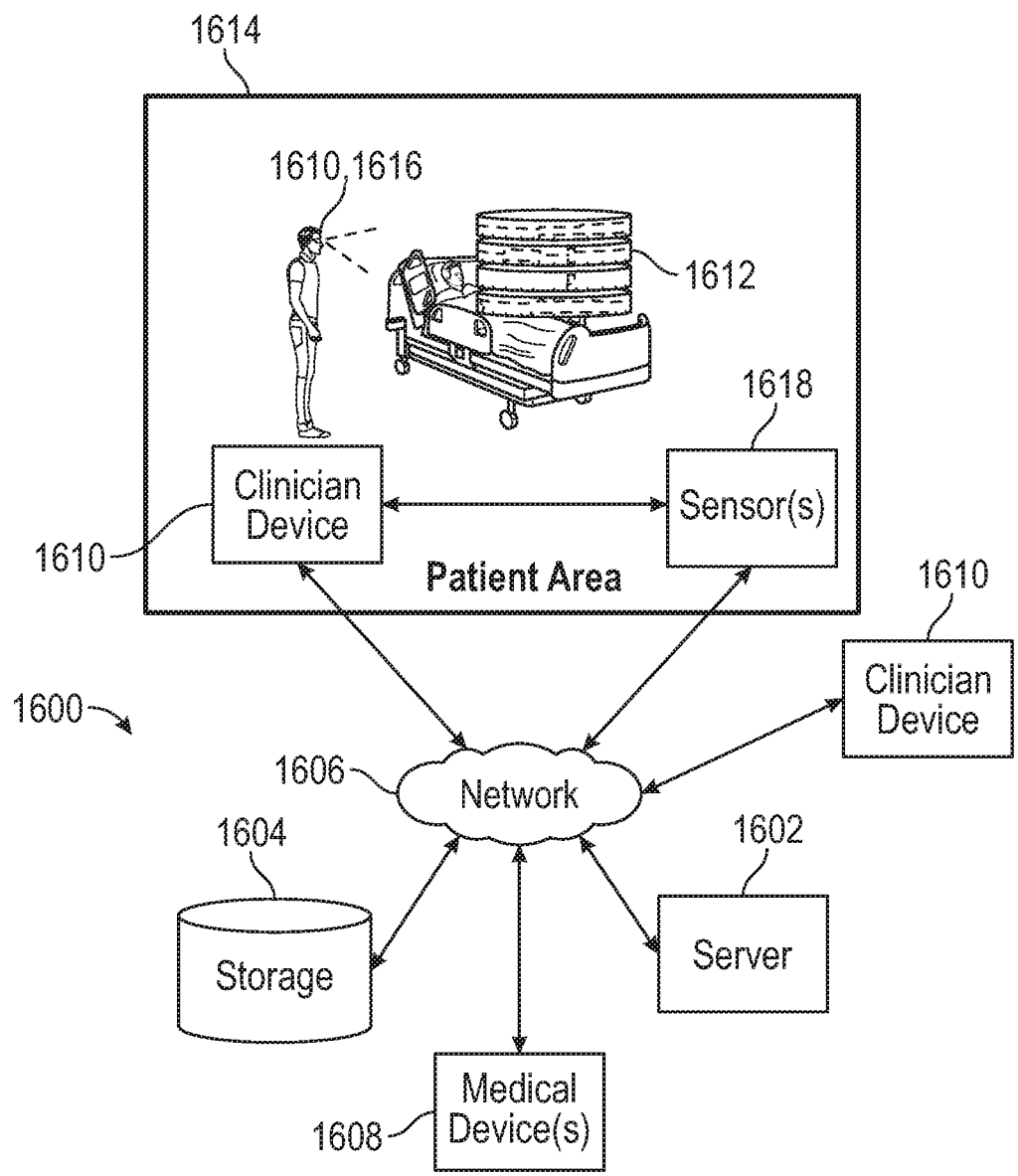
FIG. 16 is a conceptual diagram illustrating an example server-client system for providing the disclosed virtual reality interface for the display of patient health data, according to various aspects of the subject technology.

FIG. 16 is a conceptual diagram illustrating an example distributed server-client system 1600 for providing the disclosed virtual reality interface for the display of patient health data, according to various aspects of the subject technology. System 1600 includes (among other equipment) a centralized server 1602 and at least one data storage location 1604. Centralized server 1602 and data storage(s) 1604 may include multiple computing devices distributed over a local or wide area network 1606, or may be combined in a single device. Patient data may be received, for example, from one or more medical devices 1608 that communicate patient data, over network 1606, to centralized server 1602 in real time as the data is collected or measured from the patient at various locations in a healthcare organization. Centralized server 1602 may store the patient data in real time in data source(s) 1604.

According to various implementations, centralized server 1602 is configured to (by way of instructions) generate and provide virtual interface 100 to clinician devices 1610. In some implementations, centralized server 1602 may function as a web server, and virtual interface 100 may rendered from a website provided by server 1602. According to various implementations, centralized server 1602 may aggregate real time patient data (e.g., from data storage 1604) and provide the data for display in virtual interface 100. The data and/or virtual interface 100 may be provided (e.g., transmitted) to each clinician device 1610, and each clinician device 1610 may include a software client program or other instructions configured to, when executed by one or more processors of the device, render and display virtual interface 100 with the corresponding data. The depicted clinician devices 1610 may include personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

According to some implementations, the disclosed 3D cylindrical structures 1612 of virtual interface 100 may be viewed as part of an augmented reality, for example, as a holographic set of cylinders stacked over a location within a room 1614. As described previously, a representation of the body (or relevant portion thereof) may be displayed within the cylinder structure. Clinicians in the room may view the cylindrical structure through a set of augmented reality glasses (or goggles) 1616 (which may be part of or connected to a clinician device 1610), or by way of a camera interface of a clinician device 1610. An augmented reality device 1616 include various hardware devices, such as a head-mounted display that places images of both the physical world and virtual objects over the user's field of view, eyeglasses that employ cameras to intercept the real world view and re-display an augmented view through the eyeglass, a heads-up display, contact lenses that contain elements for display embedded in to the lens, virtual retinal display in which a display is scanned directly onto the retina or a user, an eye tap, that intercepts light and augments light that passes through the center of the lens of the eye of the wearer, and other similar devices.

A virtual reality enabled system to augment the disclosed interface for multiple users may include one or more sensors. For example, the system 1600 may include one or more positional sensors 1618 that detect individuals and related motion within the room 1614, and that detect gestures made by the individuals within the room and translate the gestures to within the virtual 3D space of the 3D cylindrical structure. The sensors may be configured to map a position of a user object using x, y and z axis coordinates so as to identify a common location between two users. The sensors may then be configured to map a position of each user in the space using location information generated from user devices (e.g., mobile device or augmented reality device), so as to generate a viewing region and corresponding perspective view for each user in the three-dimensional space. The computer may the differentiate between two or more active regions within the space to display the appropriate image to each participant.

In some implementations, clinician devices 1610 may include wearable devices to sense gestures and movements of clinicians. The system may be configured to receive motion data (e.g., gyroscope or accelerometer data) from a wearable or other mobile device associated with a clinician (e.g., the clinician's smart phone or tablet, or virtual reality glasses), and to determine from the motion data the intended gestures and/or movements of the clinicians. In this manner, each clinician (or a designated clinician) may use physical gestures to manipulate the cylinders (or other related structures) within the 3D space as if those cylinders (or structures) were physical structures, and the manipulations may be visualized by all clinicians viewing the 3D space (e.g., using augmented reality glasses or goggles or a computing device). Similarly, manipulations of structures within the 3D space by way of a computer interface (e.g., on a mobile device) may also be visualized by the clinicians using augmented reality.

Each clinician may view (e.g., on a computing device or through augmented reality glasses) the same portion of the virtual interface 100, or a portion of the interface that may be viewable from the user's perspective had the three dimensional interface actually existed in the real world. In a manner similar to the use of a Lazy Susan to rotate food around a table, a user can rotate data on the cylindrical structure around the displayed object representation. Alternative manipulations of elements or data can include pushing or passing elements across the cylinder. In the absence of tablets or glasses, it should also be appreciated that holographic projection of the visual cylindrical health data element or elements and other means of two and three-dimensional presentation forms are possible.

According to some implementations, one or more cylinders of data may appear over top of the patient (e.g., in an operating room). Clinicians of different specialties within the room may view and manipulate the cylinders to share data as a group. For example, one clinician could rotate a cylinder of data to pass data to another clinician as if using a Lazy Susan. The other clinician may flag certain data and then pass the flagged data back to the first clinician by rotating the cylinder in the opposite direction, or by continuing the rotation to a full 360 degrees. A clinician may also expand data on a cylinder or raise the cylinder into the air for all clinicians viewing the 3D space to see.

In some implementations, system 1600 and virtual interface 100 make use of either device camera input or visual cues from, for example, augmented reality glasses to self-select data sources for display on the cylindrical health data element. For example, system 1600 may collect real time motion data from the various clinician devices 1610, 1616 and sensors 1618. If, based on this data, system 1600 detects that a user points a camera on a tablet at a ventilator or other medical device, or looks at an infusion pump/device with visual tools, such as augmented reality glasses 1616, the system may display relevant data from said device in virtual interface 100 (e.g., on the visual cylindrical health data element for the individual patient or the population-centric view). In some implementations, system 1600 may automatically detect such machine or device based on image recognition or its known geolocation. Furthermore, augmented reality interactions can enable enhanced viewing of radiographs or other imaging-based health data by enabling larger viewing access. For example, a user viewing an x-ray on the health cylinder can move a clinician device 1610 such as a tablet around in space to see a larger view of the x-ray or alternatively utilize AR glasses to view the x-ray on the cylinder in an enlarged manner. In another aspect of this disclosure, cross-functional discussion of patient status is enhanced by enabling a presenter of the healthcare team to discuss the patient and simultaneously navigate the displays or augmented reality as seen by other members of the healthcare team through a review of the patient status. This functionality can be transferred to other members of the healthcare team in turn to facilitate cross-functional review and coordination of care for the patient. These transitions and control functions may involve manipulation of the cylindrical health data element, time-aligned events and other visual functions in this disclosure.

Figure 17:
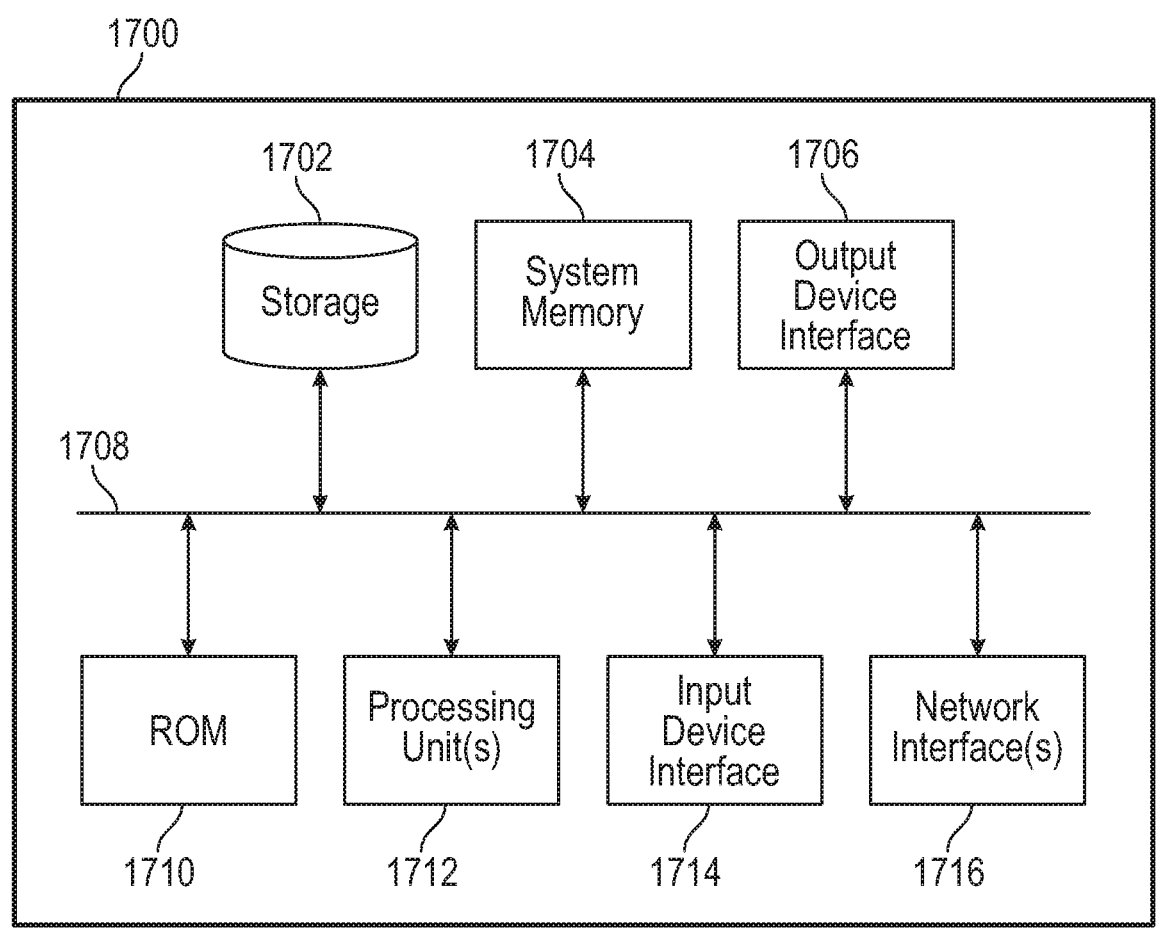
FIG. 17 is a conceptual diagram illustrating an example electronic system for generating a virtual reality interface for the display of patient health data, according to various aspects of the subject technology.

FIG. 17 is a conceptual diagram illustrating an example electronic system 1700 for generating a virtual reality interface for the display of patient health data, according to aspects of the subject technology. Electronic system 1700 may be a computing device for execution of software associated with one or more portions or steps of process 1500, or components and processes provided by FIGS. 1-16.

Electronic system 1700 may be representative, in combination with the disclosure regarding FIGS. 1-16, of the centralized server 1602 or the clinician device(s) 1610, 1616 described above. In this regard, electronic system 1700 or computing device may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 1700 may include various types of computer readable media and interfaces for various other types of computer readable media. In the depicted example, electronic system 1700 includes a bus 1708, processing unit(s) 1712, a system memory 1704, a read-only memory (ROM) 1710, a permanent storage device 1702, an input device interface 1714, an output device interface 1706, and one or more network interfaces 1716. In some implementations, electronic system 1700 may include or be integrated with other computing devices or circuitry for operation of the various components and processes previously described.

Bus 1708 collectively represents all system, peripheral, and chipset buses that communicatively connect the numerous internal devices of electronic system 1700. For instance, bus 1708 communicatively connects processing unit(s) 1712 with ROM 1710, system memory 1704, and permanent storage device 1702.

From these various memory units, processing unit(s) 1712 retrieves instructions to execute and data to process in order to execute the processes of the subject disclosure. The processing unit(s) can be a single processor or a multi-core processor in different implementations.

ROM 1710 stores static data and instructions that are needed by processing unit(s) 1712 and other modules of the electronic system. Permanent storage device 1702, on the other hand, is a read-and-write memory device. This device is a non-volatile memory unit that stores instructions and data even when electronic system 1700 is off. Some implementations of the subject disclosure use a mass-storage device (such as a magnetic or optical disk and its corresponding disk drive) as permanent storage device 1702.

Other implementations use a removable storage device (such as a floppy disk, flash drive, and its corresponding disk drive) as permanent storage device 1702. Like permanent storage device 1702, system memory 1704 is a read-and-write memory device. However, unlike storage device 1702, system memory 1704 is a volatile read-and-write memory, such a random access memory. System memory 1704 stores some of the instructions and data that the processor needs at runtime. In some implementations, the processes of the subject disclosure are stored in system memory 1704, permanent storage device 1702, and/or ROM 1710. From these various memory units, processing unit(s) 1712 retrieves instructions to execute and data to process in order to execute the processes of some implementations.

Bus 1708 also connects to input and output device interfaces 1714 and 1706. Input device interface 1714 enables the user to communicate information and select commands to the electronic system. Input devices used with input device interface 1714 include, e.g., alphanumeric keyboards and pointing devices (also called "cursor control devices"). Output device interfaces 1706 enables, e.g., the display of images generated by the electronic system 1700. Output devices used with output device interface 1706 include, e.g., printers and display devices, such as cathode ray tubes (CRT) or liquid crystal displays (LCD). Some implementations include devices such as a touchscreen that functions as both input and output devices.

Also, as shown in FIG. 17, bus 1708 also couples electronic system 1700 to a network (not shown) through network interfaces 1716. Network interfaces 1716 may include, e.g., a wireless access point (e.g., Bluetooth or WiFi) or radio circuitry for connecting to a wireless access point. Network interfaces 1716 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 1700 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U. S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method for generating a virtual reality interface to display patient health data, comprising:

generating and displaying, in a three-dimensional space including an object representation, one or more curvilinear bands floating within the three-dimensional space at least partially circumscribing the object representation and being vertically separated from each other by an open space, and each being configured for a continuous presentation of data versus time;

displaying, along a curvilinear surface of each of the curvilinear bands, respective two-dimensional data representations of first physiological data;

receiving a first user selection of a respective band of the curvilinear bands;

generating, in response to receiving the first user selection, one or more additional curvilinear bands floating within the three-dimensional space and partially circumscribing the object representation above or below the selected respective band of the curvilinear bands; and displaying, on a curvilinear surface of a respective curvilinear band of the one or more additional curvilinear bands, a two-dimensional data representation of second physiological data associated with the data displayed on the curvilinear surface of the selected respective band of the curvilinear bands.

2. The method of claim 1, further comprising:

receiving ventilation data for a patient receiving ventilation from a ventilator, wherein displaying at least one of the respective two-dimensional data representations comprises a displaying a visualization of ventilation data verses time on the curvilinear surface of a respective curvilinear band.

3. The method of claim 1, wherein at least one band of the one or more curvilinear bands comprises an image viewing dialog configured to display images associated with a patient, and the two-dimensional data representation of the first or second physiological data comprises a first image associated with the patient, the method comprising:

receiving a second user selection to view the image viewing dialog based on an interaction with the at least one band;

generating, in response to receiving a second user selection to view the image viewing dialog, the image viewing dialog floating within the three-dimensional space, the image viewing dialog comprising an image viewing area displaying the first image, and circumscribed by multiple icons representative of selectors for other images to display in the image viewing area;

receiving an icon selection of one of the multiple icons; and displaying, response to the icon selection, a second image in the image viewing area.

4. The method of claim 1, further comprising:

determining an occurrence of an event based at least in part on at least one of the first physiological data;

generating a different representation of the occurrence of the event for including in a respective two-dimensional data representation of the first physiological data, wherein the different representation of the occurrence of the event comprises a two-dimensional shape that is overlaid along a portion of the respective two-dimensional data representation of the first physiological data coinciding with the occurrence of the event;

receiving a second user selection of the portion of the respective two-dimensional data representation of the first physiological data coinciding with the occurrence of the event; and in response to the second user selection, generating a data visualization associated with the portion of the respective two-dimensional data representation of the first physiological data and the event.

5. The method of claim 1, further comprising:

displaying a first curvilinear band and a second curvilinear band as vertically aligned in time and time-locked such that if the first and second curvilinear bands are viewed together and one is rotated to scroll through time, the other will rotate along with it so that events occurring on each surface are viewed together at the same time.

6. The method of claim 1, further comprising:

providing, to an augmented reality device, a virtual interface comprising the three-dimensional space augmented with a real-world visualization, wherein the three-dimensional space is generated as part of an augmented reality, and the object representation and the one or more curvilinear bands are floating in the augmented reality in relation to at least one physical object outside of the augmented reality.

7. The method of claim 6, further comprising:

mapping the object representation to a location of a patient in a medical facility; and displaying to a user, using the augmented reality device, the object representation at the location of the patient, wherein displaying respective two-dimensional data representations of first physiological data comprises displaying data associated with the patient.

8. The method of claim 6, further comprising:

receiving motion data from one or more motion sensors; and detecting, based on the motion data received from the one or more motion sensors, a physical gesture performed by a user in a physical space associated with the augmented reality, wherein the first user selection is received responsive to the physical gesture matching a predetermined gesture for selecting a portion of the curvilinear bands.

9. The method of claim 6, further comprising:

receiving a respective location for each of a plurality of users;

mapping the object representation to a location between at least two users of the plurality of users;

displaying, via respective augmented reality devices associated with the at least two users, the object representation, at the mapped location, to the at least two users; and providing the virtual interface to the respective augmented reality devices, each user receiving a different perspective of the object representation and the one or more curvilinear bands based on the user's respective location.

10. The method of claim 9, further comprising:

receiving an indication of a gesture by a first user of the plurality of users to rotate a first band of the curvilinear bands in a direction towards a second user of the plurality of users; and displaying, in the respective augmented reality devices of the at least two users, the first band as rotating in the direction toward the second user such as to pass data on a surface of the first band adjacent the first user to the second user by way of the first band being rotated toward the second user.

11. A system comprising:

one or more processors;

a memory device containing instructions which, when executed by the one or more processors, cause the one or more processors to perform operations comprising:

generating and displaying, in a three-dimensional space including an object representation, one or more curvilinear bands floating within the three-dimensional space at least partially circumscribing the object representation and being vertically separated from each other by an open space, and each being configured for a continuous presentation of data versus time;

displaying, along a curvilinear surface of each of the curvilinear bands, respective two-dimensional data representations of first physiological data;

receiving a first user selection of a respective band of the curvilinear bands;

generating, in response to receiving the first user selection, one or more additional curvilinear bands floating within the three-dimensional space and partially circumscribing the object representation above or below the selected respective band of the curvilinear bands; and displaying, on a curvilinear surface of a respective curvilinear band of the one or more additional curvilinear bands, a two-dimensional data representation of second physiological data associated with the data displayed on the curvilinear surface of the selected respective band of the curvilinear bands.

12. The system of claim 11, wherein the operations further comprise:

receiving ventilation data for a patient receiving ventilation from a ventilator, wherein displaying at least one of the respective two-dimensional data representations comprises a displaying a visualization of ventilation data verses time on the curvilinear surface of a respective curvilinear band.

13. The system of claim 11, wherein the operations further comprise:

determining an occurrence of an event based at least in part on at least one of the first physiological data;

generating a different representation of the occurrence of the event for including in a respective two-dimensional data representation of the first physiological data, wherein the different representation of the occurrence of the event comprises a two-dimensional shape that is overlaid along a portion of the respective two-dimensional data representation of the first physiological data coinciding with the occurrence of the event;

receiving a second user selection of the portion of the respective two-dimensional data representation of the first physiological data coinciding with the occurrence of the event; and in response to the second user selection, generating a data visualization associated with the portion of the respective two-dimensional data representation of the first physiological data and the event.

14. The system of claim 11, wherein the operations further comprise:

displaying a first curvilinear band and a second curvilinear band as vertically aligned in time and time-locked such that if the first and second curvilinear bands are viewed together and one is rotated to scroll through time, the other will rotate along with it so that events occurring on each surface are viewed together at the same time.

15. The system of claim 11, wherein the operations further comprise:

providing, to an augmented reality device, a virtual interface comprising the three-dimensional space augmented with a real-world visualization, wherein the three-dimensional space is generated as part of an augmented reality, and the object representation and the one or more curvilinear bands are floating in the augmented reality in relation to at least one physical object outside of the augmented reality.

16. The system of claim 15, wherein the operations further comprise:

mapping the object representation to a location of a patient in a medical facility; and displaying to a user, using the augmented reality device, the object representation at the location of the patient, wherein displaying respective two-dimensional data representations of first physiological data comprises displaying data associated with the patient.

17. The system of claim 15, wherein the operations further comprise:

receiving motion data from one or more motion sensors; and detecting, based on the motion data received from the one or more motion sensors, a physical gesture performed by a user in a physical space associated with the augmented reality, wherein the first user selection is received responsive to the physical gesture matching a predetermined gesture for selecting a portion of the curvilinear bands.

18. The system of claim 15, wherein the operations further comprise:

receiving a respective location for each of a plurality of users;

mapping the object representation to a location between at least two users of the plurality of users;

displaying, via respective augmented reality devices associated with the at least to users, the object representation, at the mapped location, to the at least two users; and providing the virtual interface to the respective augmented reality devices, each user receiving a different perspective of the object representation and the one or more curvilinear bands based on the user's respective location.

19. The system of claim 18, wherein the operations further comprise:

receiving an indication of a gesture by a first user of the plurality of users to rotate a first band of the curvilinear bands in a direction towards a second user of the plurality of users; and displaying, in the respective augmented reality devices of the at least two users, the first band as rotating in the direction toward the second user such as to pass data on a surface of the first band adjacent the first user to the second user by way of the first band being rotated toward the second user.

20. A non-transitory computer-readable medium comprising instructions, which when executed by a computing device, cause the computing device to perform operations comprising:

generating and displaying, in a three-dimensional space including an object representation, one or more curvilinear bands floating within the three-dimensional space at least partially circumscribing the object representation and being vertically separated from each other by an open space, and each being configured for a continuous presentation of data versus time;

displaying, along a curvilinear surface of each of the curvilinear bands, respective two-dimensional data representations of first physiological data;

receiving a first user selection of a respective band of the curvilinear bands;

generating, in response to receiving the first user selection, one or more additional curvilinear bands floating within the three-dimensional space and partially circumscribing the object representation above or below the selected respective band of the curvilinear bands; and displaying, on a curvilinear surface of a respective curvilinear band of the one or more additional curvilinear bands, a two-dimensional data representation of second physiological data associated with the data displayed on the curvilinear surface of the selected respective band of the curvilinear bands.

* * * * *